United States Patent
Van Broeckhoven et al.

[19]

[11] Patent Number: 6,110,670
[45] Date of Patent: Aug. 29, 2000

[54] NUCLEOTIDE SEQUENCES, PROBES AND A PROCESS FOR THE IN VITRO DIAGNOSIS OF CHROMOSOMAL ANOMALIES CORRELATED WITH CMT1A DISEASE

[75] Inventors: Christine Van Broeckhoven; Peter Raeymaekers, both of Antwerp; Peter De Jonghe, Edegem; Jean-Jacques Martin, Antwerp, all of Belgium

[73] Assignee: N.V. Innogenetics S.A., Ghent, Belgium

[21] Appl. No.: 08/808,032

[22] Filed: Mar. 4, 1997

Related U.S. Application Data

[62] Continuation of application No. 08/617,428, Mar. 18, 1996, abandoned, which is a continuation of application No. 08/146,085, filed as application No. PCT/EP92/01026, May 6, 1992.

[30] Foreign Application Priority Data

May 7, 1991 [EP] European Pat. Off. .............. 91401220

[51] Int. Cl.$^7$ .............................. C12Q 1/68; C07H 21/00
[52] U.S. Cl ........................... 435/6; 536/23.1; 536/24.1; 536/24.3; 536/24.31; 536/24.32; 536/24.33
[58] Field of Search .................... 435/6, 810; 436/501; 536/23.1, 24.1, 24.5, 24.33; 935/77, 78

[56] References Cited

U.S. PATENT DOCUMENTS

| 5,306,616 | 4/1994 | Lupski et al. | 435/6 |
| 5,599,920 | 2/1997 | Patel et al. | 536/23.5 |

FOREIGN PATENT DOCUMENTS

WO 92/21694  12/1992  WIPO.

OTHER PUBLICATIONS

Raeymaekers et al., Neuromuscular Disorders, vol. 1, No. 2, pp. 93–97, 1991.
By E. Wright et al., "A Genetic Map of Human Chromosome 17p", Genomics, 1990, vol. 7, pp. 103–109.

By J. Vance et al., "Localization of Charcot–Marie–Tooth Disease Type 1a (CMT1A) to Chromosme 17p11.2", Genomics, 1991, vol. 9, pp. 623–628.

By R. Magenis et al., "De novo partial duplication of 17p", National Library Of Medicine, 1986, vol. 24, pp. 415–420.

By V. Timmerman et al., "Assignment of the Charcot–Marie–Tooth Neuropathy Type 1 (CMT 1a) Gene to 17p11.2–p12", American Journal of Genetics, 1990, vol. 47, pp. 680–685.

By R. White et al., "Construction of linkage maps with DNA markers for human chromosomes", Nature, Jan. 1985, vol. 313, No. 10, pp. 101–105.

By H. Kazazian, Jr., "Gene Probes: Application to Prenatal and Postnatal Diagnosis of Genetic Disease", Clinical Chemistry, 1985, vol. 31, No. 9, pp. 1509–1513.

(List continued on next page.)

*Primary Examiner*—Ardin H. Marschel
*Attorney, Agent, or Firm*—Young & Thompson

[57] ABSTRACT

The invention relates to a process for the in-vitro diagnosis of chromosomal anomalies liable to be correlated with CMT1a disease. The invention also relates to probes intended in this in-vitro diagnosis process and to kits containing said probes. The probes of the invention can contain a sequence constituted of from about 15 successive nucleotides of a Not1 fragment, with said Not1 fragment having $1.2\times10^6$ base pairs and being obtained after digesting human DNA of patients with Not1, separating the fragments resulting from digestion by pulsed field gel electrophoresis and hybridizing the resulting fragments with any of the probes VAW409, EW401 or VAW412 or their derivatives, to about the total number of the successive nucleotides of the Not1 fragment. The probes enable the detection of the duplication of a part of chromosome 17p.

44 Claims, 11 Drawing Sheets

OTHER PUBLICATIONS

By J. Lupski et al., "DNA Duplication Associated with Charcot–Marie–Tooth Disease Type 1A", Cell, Jul. 26, 1991, vol. 66, pp. 219–232.

By P. Spreyer et al., "Axon–regulated expression of a Schwann cell transcript that is homologous to a 'growth arrest–specific' gene", The EMBO Journal, 1991, vol. 10, No. 12, pp. 3661–3668.

By P. Raemaekers et al., "Estimation of the size of the chromosome 17p11.2 duplication in Charcot–Marie–Tooth neuropathy type 1a (CMT1a)", Journal of Modern Genetics, 1992, vol. 29, pp. 5–11.

By U. Suter et al., "Trembler mouse carries a point mutation in a myelin gene", Nature, Mar. 19, 1992, vol. 356, pp. 241–244.

```
CTTTTGTAAAGTAATAATATTTGTTACTTATATATTTTCTAACTATGAAAATAACCCTACCTGATGC
AGAGTCCTAGAAAAACACAGACAAGGCCGGGTGCGGTGGCTCACACCTAATCCCTGCACTT
TGGGATGCTGAGATAGGAGGATCAGTTGAGGTCAGGAGTTCGAGACCAGCCTGACGAACATG
GTGAAXCCCGTCTCTACTAAAAATACAAAAATTAGCCAGGCATGGTGGTGGGTGCTTGTAAT
CCCAGCTACTCAGGAGGCTGAGGCAGGAGAATCACTTCGAACCTGGAAGGAGAGGTTGCAGT
GAGCCGAGATTGGCCACTGCCACTCCAGCCTGGGTGACAGAGTGAGACTCTGTCTCAAAAA
AGAAAAAAAGAAAACACAGACAAGCCACAAGTGCCATGTATAGCATGCCCTGGATGC
TGTGGGATACAGGCTGAAAACAGCTTGATGCCTTTCCTACCACAGCTTGTTCAACTTACCCC
ACCAGTGGTTCTTTGCCAGGCCCCTGGATGCAATTTGGGCAGGATCCATGGTCTCTTCCA
GCCACTTTCTTAAAAGTTAACTTGATTGAAATCACATACCATACAATGCACGCAGTTGA
AATATAGCCTGTCTGATTTTTCAGTAACATTGTCTGTAAAATAAATATCTACTTTAACATGA
ATTTGCCTGGTATATGGATTACTTTTTTGAATGTACCATAATCAACCTTTTTGTTTTAAACT
TTTGAGCATTAGGTAGTTTCTCATTTTCAGGGATCAGCATAAATATGGCTGAAATGAATA
TCCTCACACGTATATCCTTGGTACATTGTTTCTTATAATACATTTCTAGAAGTGGAAGTTC
TGGGTTTTCCACATTTGAATGAAAGGCTGTGTTGTTGTGCCTCTTTACCCTCCAGGAAG
GTTGTACCAATTCAACATTCATCTCTGTATTATACAGAGAAACTTTTTCTAAATATGCTCGC
CAGCACTGCAAATGATCATTCTCTACTCCTGCTAATATTCCTTAGTAGGCTGTTTTCAT
```

Figure 1

TAATGCTTCTCTTTGATTAGCCCCTGAGGCTGAGTATTTGTCATATGGCTTATTGATGTGATG
TGTGACACATTTATAATGAACCTACACGTTCACATCATTCATTAATCCTTTTGCCCCTTGA
AACTGGCAGAAGAAGCCAGCTTACGCTTTAGATAAATAGAAAACTGATTAGCAGTAAATAA
GGATAATTAAGGAAAGTTGAAAATAAGCCTCATTCTGATATTCACATTTATATATGAAGCT
AGGATCAGGACCTGGGGGTTTCTCTCTCTCAGGATAAATGATTGCCTAGCCGATCCTGTAGG
CTGATTCATCACTCTCACTGTGTCTTGTCTCTCTCTTTTCAGTGTCTCAGTGCCTGA
GTCCTGGGCCAAATTTACAGATGACATATTCTCCGCTCCCAGAGTGAACGGGCAGCTTCGCT
AAGCTAAGAGACGACATTGAAAACCTCTGGTTGTGACTGCCAATGAGATGTGAATCAATT
CAACAAAGTGAACTTGTCTTTCACCAATGCGATGCTGAGACTGCAGATGCTAAGAATAAGA
TTCAGACGCCACTTAGCAAAGTAAATCTCTCACCACTCCCAGTGTACCCCTTAGCTGACCTGGACAG
AGCGGTGTGCTCTGGGACTACAAATCTCCACCACTCCCAGAGAGGCACCATAGGCATGTGA
CAGCCCTGGCCACACAGAGCAAGAAAATTTAAACAGCACACAAAGCATGCCATTTATTCAGC
CAGGTAGCCAGGTGTCAAATGAATCCACTGGTATTGGAACACAAAGAAGGCAC
TATGTAATGAAAAGTTCTAGTTCTTTAATAGAACAAAAATATTATTATTAAAGTTTAATGG
ATCGCTGTATATAACTAGGAAGTGAATTTATTATTAGAACATATGGTAGAAATGTTTCTGT
TAAAGTATTTTAGACCCCTTTTCTGAATACAAAACCAAATACAGGAAACCAAATAAGAGTTTAGGTAGTT
CAAAGTGTTTCTGATATTGAAAATTTTAAGTGCTGAAAGCATAAGAGTTTTACAATGACTA
CAAAATGAAGGAGTCCAGCAGAATT

Figure 1 (suite)

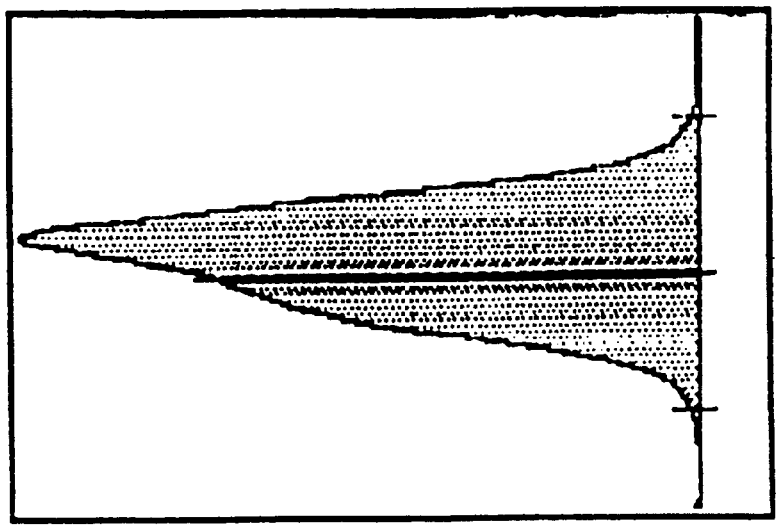
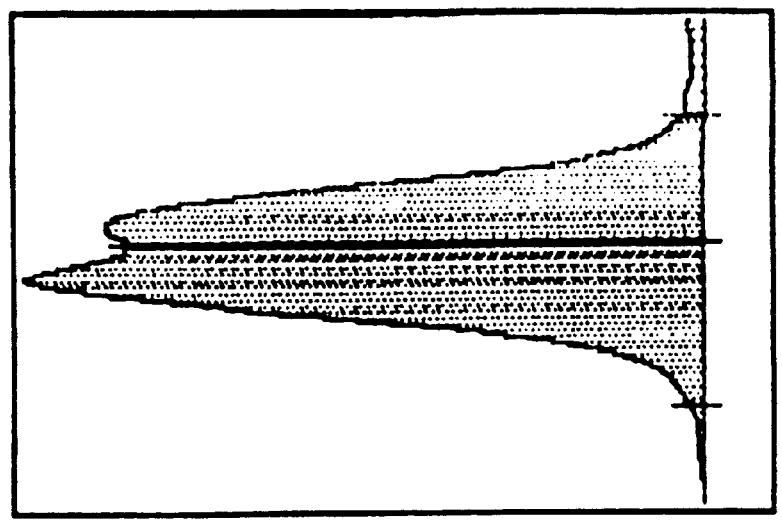
C
Figure 2 (suite)

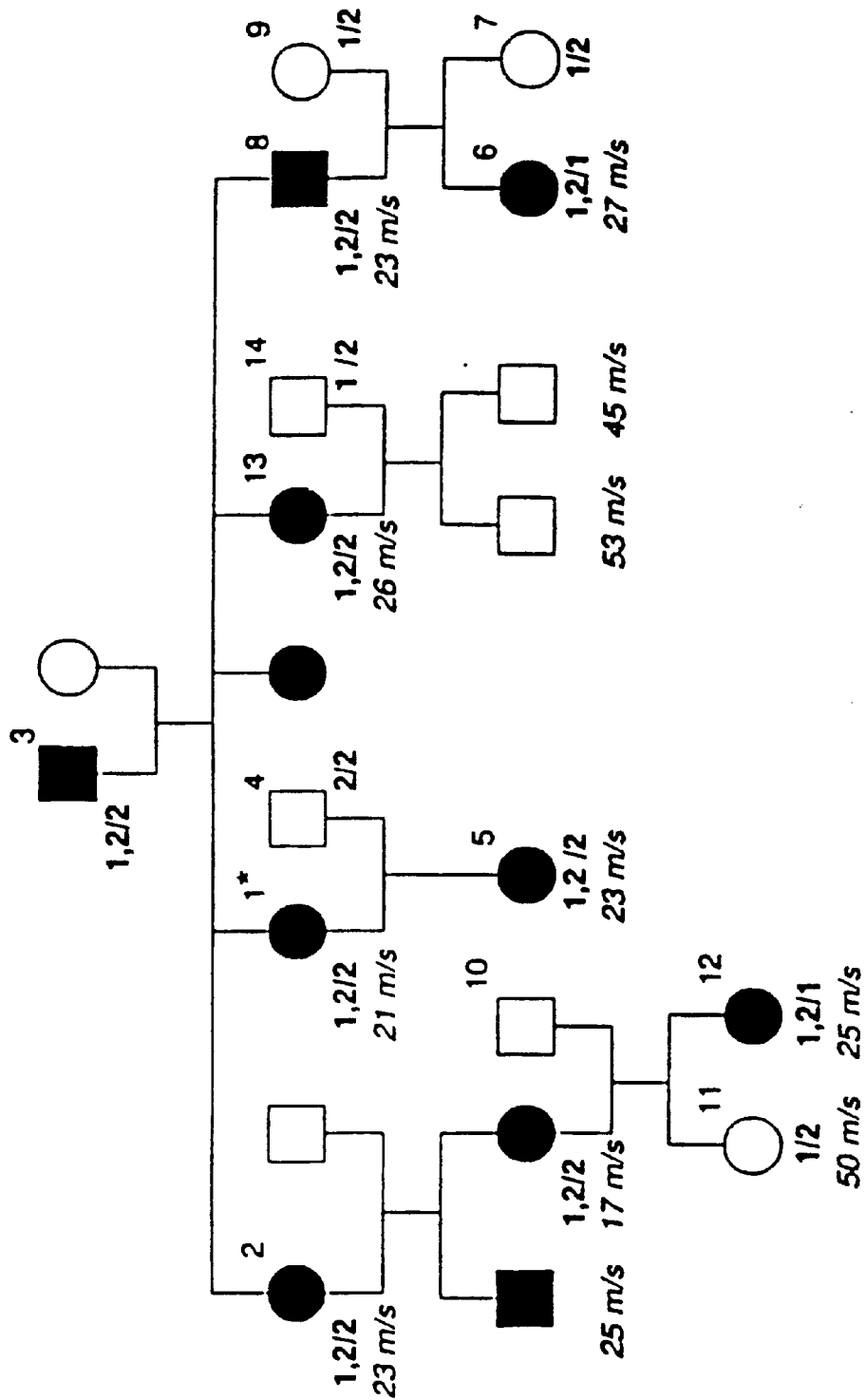
Figure 3 (suite)

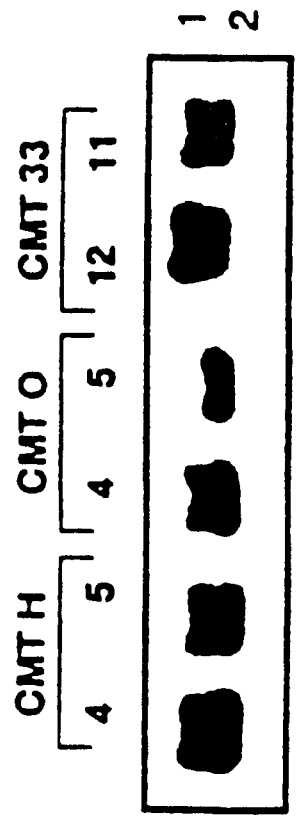
Figure 3 (suite)

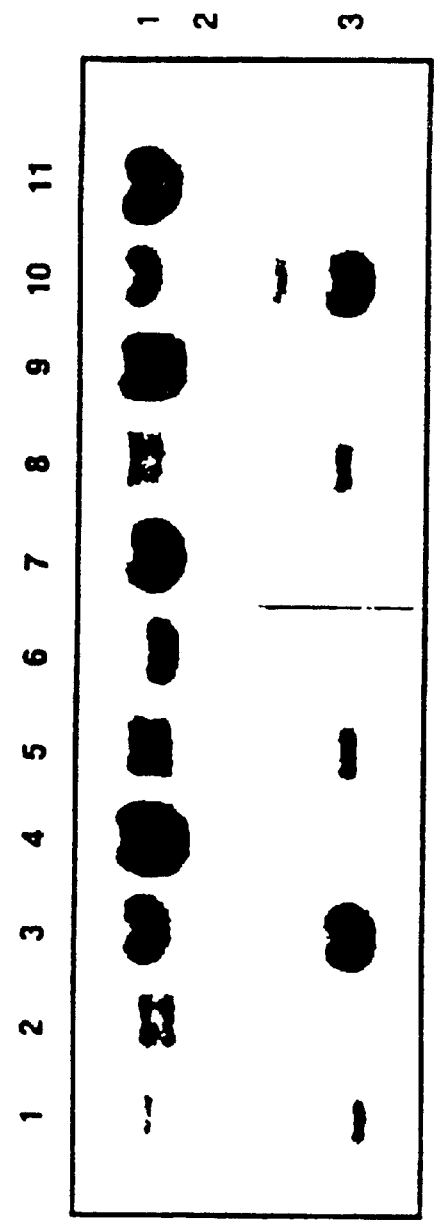
Figure 4 (suite)

NUCLEOTIDE SEQUENCES, PROBES AND A PROCESS FOR THE IN VITRO DIAGNOSIS OF CHROMOSOMAL ANOMALIES CORRELATED WITH CMT1A DISEASE

This application is a continuation of application Ser. No. 08/617,428, filed Mar. 18, 1996 now abandoned, which is a continuation of Ser. No. 08/146,085, filed Nov. 8, 1993, now abandoned, which is a 371 filing of PCT/EP92/010,26; filed May 6, 1992.

The invention relates to a process for the in vitro diagnosis of chromosomal anomalies correlated with CMT1a disease.

The invention also relates to probes which can be used in the in vitro diagnosis process and to kits containing the probes.

Charcot-Marie-Tooth type 1 (CMT1) or hereditary motor and sensory neuropathy type I (HMSN I) is a disease of the peripheral nervous system affecting the lower distal limb muscles and nerves. Although most CMT1 patients inherit the disease, sporadic cases have been observed. Familial CMT1 disease is genetically heterogeneous with loci located on chromosomes X, 1 and 17. A major gene locus for autosomal dominant CMT1 (CMT1a) is localized on chromosome 17p (Vance J. M. et al., 1989, "Linkage of Charcot-Marie-Tooth neuropathy type Ia to chromosome 17", Experimental Neurology 104:1–4; Raeymaekers P. et al., 1989, "Localization of the mutation in an extended family with Charcot-Marie-Tooth neuropathy (HMSN I)", Am. J. Hum. Genet. 45:953–958; Middleton-Price H. R. et al., 1990, "Linkage of hereditary motor and sensory neuropathy type I to the pericentromeric region of chromosome 17", Am. J. Hum. Genet. 46:92–94; Patel P. I. et al., 1990, "Isolation of a marker linked to the Charcot-Marie-Tooth disease type 1 a gene by differential Alu-PCR of human chromosome 17-retaining hybrids", Am. J. Hum. Genet. 47:926–934; Timmerman V. et al., 1990, "Assignment of the Charcot-Marie-Tooth neuropathy type I (CMT1a) gene to chromosome 17p11.2–p12", Am. J. Hum. Genet. 47:680–685; Chance P. F. et al., 1990, "Genetic linkage and heterogeneity in type I Charcot-Marie-Tooth disease (Hereditary motor and sensory neuropathy type I)", Am. J. Hum. Genet. 47:915–925; McAlpine P. J. et al., 1990, "Localization of a locus for Charcot-Marie-Tooth neuropathy type Ia (CMT1a) to chromosome 17", Genomics 7:408–415 and Defesche J. C. et al., 1990, "Genetic linkage of hereditary motor and sensory neuropathy type I (Charcot-Marie-Tooth disease) to markers of chromosome 1 and 17", Neurology 40:1450–1453).

Both the sporadic and familial CMT1 patients have a homogeneous disease phenotype characterized by progressive weakness and atrophy of distal limb muscles, pes cavus, depressed or absent deep tendon reflexes and markedly reduced nerve conduction velocities (NCV) (Dyck, P. J. et al. in Peripheral Neuropathy p. 1600–1642, Saunders, Philadelphia, 1984). Peripheral nerve biopsies in CMT1 patients consistently showed a segmental pattern of extensive de- and remyelination of both motor and sensory nerves resulting in onion bulb formations. Although in CMT1 families both autosomal recessive and X-linked forms have been reported, most CMT1 patients inherited the disease in an autosomal dominant manner. In autosomal dominant CMT1 families genetic heterogeneity has been documented by linkage studies. In some families, designated CMT1b, suggestive linkage was observed with the Duffy blood group located on chromosome 1g (Bird T. D. et al., 1982, Am. J. Hum. Genet. 34:388–394; Chance P. F. et al., 1990, Am. J. Hum. Genet. 47:915–925; Defesche J. C. et al., 1990, Neurology 40:1450–1453). However, in only one CMT1b pedigree was conclusive evidence for linkage to the Duffy blood group obtained (Stebbins N. B. et al., 1982, Am. J. Hun. Genet. 34:195A). In the latter pedigree, tight linkage to the FC gamma RII gene located in 1g21.2–g23 was reported recently (Lebo R. et al., 1990, J. Neurol. Sci. 98:A106). In a large number of families, designated CMT1a, conclusive linkage was detected with two pericentromeric chromosome 17p markers pEW301 (D17S58) and pAT10-41 (D17S71) indicating that chromosome 17p carries a major gene locus for CMT1 disease (Chance P. F. et al., 1990, Am. J. Hum. Genet. 47:915–925; Defesche J. C. et al., 1990, Neurology 40:1450–1453; Vance J. M. et al., 1989, Exp. Neurol. 104:186–189; Raeymaekers P. et al., 1989, Am. J. Hum. Genet. 45:953–958; Middleton-Price H. R. et al., 1990, Am. J. Hum. Genet. 46:92–94; McAlpine P. J. et al., 1990, Genomics 7:408–415; Patel P. I. et al., 1990, Am. J. Hum. Genet. 47:926–934).

Markers VAW409, VAW412 and EW401, their physical and genetic locations, as well as their polymorphisms, have been published in Wright E. C. et al. "A genetic Map of Human Chromosome 17p" Genomics 7:103–109 (1990); in Wright E. C. et al. "Genetic linkage map of chromosome 17p" Cytogenet. Cell Genet. 51:1110 (1989); in Barker D. et al. 32 "New chromosomes 17 DNA markers" Cytogenet. Cell Genet. 46:576 (1987); in Vance J. M. et al. "Localization of Charcot-Marie-Tooth Disease Type 1a (CMT1A) to Chromosome 17p11.2" Genomics 9:623–628 (1991). However, although these markers have been used for genetic linkage studies, they have not been used as probes for the direct in vitro diagnosis of CMT1a. To date, the chromosomal alteration(s) responsible for the clinical symptoms of CMT1 disease have not been unequivocally identified.

So far, there is no in vitro diagnostic means for detecting the disease.

One of the aspects of the invention is to provide a direct in vitro diagnostic process for detecting CMT1a disease.

Another aspect of the invention is to provide probes intended for the diagnosis of CMT1a disease.

Yet another aspect of the invention is to provide a kit for the in vitro diagnosis of CMT1a disease.

Still another aspect of the invention is to provide a transgenic animal, in the genome of which one or more genes encoding a peripheral myelin protein-22 (PMP-22) have been inserted, whereby the animal overproduces the PMP-22 protein and therefore can serve as a pathological model for research into CMT1a disease and its symptoms in humans and for the isolation of transgenic cells useful for immortalization and for drug study.

The invention relates to a probe for the in vitro diagnosis of patients, particularly CMT1 patients (as well as patients manifesting symptoms of CMT1 disease), presenting an alteration on their chromosome 17p, which can be correlated with the fact that they manifest the symptoms of CMT1a disease or that they could develop the symptoms of said disease, with said probe containing a sequence constituted of from about 15 successive nucleotides of NotI fragment, with said NotI fragment having $1.2 \times 10^6$ base pairs and being obtainable, preferably obtained, after digesting human DNA using NotI, separating the fragments resulting from digestion, preferably by pulsed field gel electrophoresis, and hybridizing the resulting fragments with any of the probes VAW409, pVAW409R3, pVAW409R3a, pVAW409R3b, pVAW409R1, pVAW409R1a, pVAW409R1b, pVAW409R1c, EW401, pEW401a, pEW401b, pEW401c, pEW401d, VAW412, pVAW412R3, pVAW412R3a, pVAW412R3b or pVAW412R3c, to about the total number of the successive nucleotides of the NotI fragment, or with said probe containing a sequence constituted of from about 15 successive nucleotides of the junction fragment of 500 kb (obtainable, preferably obtained, with pulsed field gel electrophoresis by digestion of human DNA of patients with SacII, AscI or FspI and hybridization with any of-the probes VAW409, pVAW409R3, pVAW409R3a, pVAW409R3b, pVAW409R1, pVAW409R1a, pVAW409R1b or pVAW409R1c) to about the total number of the successive nucleotides of the above-defined junction fragment, or with said probe containing a sequence constituted of from about 15 successive nucleotides of the junction fragment of 600 kb (obtainable, preferably obtained, with pulsed field gel electrophoresis by digestion of human DNA of patients with SfiI and hybridization with any of the probes VAW412, pVAW412R3, pVAW412R3a, pVAW412R3b, pVAW412R3c, EW401, pEW401a, pEW401b, pEW401c or pEW401d) to about the total number of the successive nucleotides of the above-defined junction fragment.

The invention also relates to probes liable to hybridize with the above-defined probes, as well as to probes which are complementary to the above-defined probes.

pVAW409R3, pVAW409R3a, pVAW409R3b, pVAW409R1, pVAW409R1a, pVAW409R1b and pVAW409R1c are the derivatives of VAW409.

pEW401a, pEW401b, pEW401c and pEW401d are the derivatives of EW401.

pVAW412R3, pVAW412R3a, pVAW412R3b and pVAW412R3c are the derivatives of VAW412.

The VAW409, VAW412 and EW401 probes and their derivatives are defined hereafter.

The invention further relates to a probe for the in vitro diagnosis of patients, particularly CMT1 patients (as well as patients manifesting symptoms of CMT1 disease), presenting an alteration on their chromosome 17p, which can be correlated with the fact that they manifest the symptoms of CMT1a disease or that they could develop the symptoms of said disease, with said probe containing a sequence constituted of from about 15 successive nucleotides of the VAW409 sequence or its derivatives, to about the total number of the successive nucleotides of the VAW409 sequence, or with said probe containing a sequence constituted of from about 15 successive nucleotides of the EW401 sequence or its derivatives to about the total number of the successive nucleotides of the EW401 sequence or its derivatives, or with said probe containing a sequence constituted of from about 15 successive nucleotides of the VAW412 sequence or its derivatives to about the total number of the successive nucleotides of the VAW412 sequence or its derivatives, or with said probe containing a sequence constituted of from about 15 successive nucleotides of any sequence of NotI fragment which is located between the following sequences: pVAW409R1, pVAW409R3, EW401 and VAW412 (with said NotI fragment having $1.2 \times 10^6$ base pairs and being obtainable, preferably obtained, after digesting human DNA with NotI, separating the fragments resulting from digestion, preferably by pulsed field gel electrophoresis, and hybridizing with any of the probes VAW409, EW401 or VAW412 or their derivatives), to about the total number of the successive nucleotides of any NotI fragment such as defined above, or with said probe containing a sequence constituted of from about 15 successive nucleotides of the junction fragment of 500 kb (obtainable, preferably obtained, with pulsed field gel electrophoresis by digestion of human DNA of patients with SacII, AscI or FspI and hybridization with probe VAW409 or its derivatives) to about the total number of the successive nucleotides of the above-defined junction fragment, or with said probe containing a sequence constituted of from about 15 successive nucleotides of the junction fragment of 600 kb (obtainable, preferably obtained, with pulsed field gel electrophoresis by digestion of human DNA of patients with SfiI and hybridization with either probe VAW412 or its derivatives or probe EW401 or its derivatives) to about the total number of the successive nucleotides of the above-defined junction fragment.

Preferred probes of the invention are pVAW409R3, pVAW409R3a, pVAW409R3b, pVAW409R1, pVAW409R1a, pVAW409R1b, pVAW409R1c, pEW401a, pEW401b, pEW401c, pEW401d, pVAW412R3, pVAW412R3a, pVAW412R3b and pVAW412R3c.

pVAW409R3a, pVAW409R3b, pVAW409R1a, pVAW409R1b, pVAW409R1c, pEW401a, pEW401b, pEW401c, pEW401d, pVAW412R3a, pVAW412R3b and pVAW412R3c are new sequences per se.

The invention still further relates to a process for the in vitro diagnosis of patients, particularly CMT1 patients (as well as patients manifesting symptoms of CMT1 disease), presenting an alteration on their chromosome 17p, which can be correlated with the fact that they manifest the symptoms of CMT1a disease or that they could develop the symptoms of said disease, which comprises the detection of a duplication of a part of chromosome 17p, simultaneously in either one of the three loci D17S122, D17S125, D17S61, or in two of them, or in all three, preferably by bringing into contact DNA (isolated from a biological sample taken from a patient) with a probe, with said probe containing a sequence constituted of from about 15 successive nucleotides of NotI fragment, with said NotI fragment having $1.2 \times 10^6$ base pairs and being obtainable, preferably obtained, after digesting human DNA with NotI, separating the fragments resulting from digestion, preferably by pulsed field gel electrophoresis, and hybridizing the resulting fragments with any of the probes VAW409, EW401 or VAW412 or their derivatives, to about the total number of the successive nucleotides of the NotI fragment, or with said probe containing a sequence constituted of from about 15 successive nucleotides of the junction fragment of 500 kb (obtainable, preferably obtained, with pulsed field gel electrophoresis by digestion of human DNA of patients with SacII, AscI or FspI and hybridization with probe VAW409 or its derivatives) to about the total number of the successive nucleotides of the above-defined junction fragment, or with said probe containing a sequence constituted of from about 15 successive nucleotides of junction fragment of 600 kb (obtainable, preferably obtained, with pulsed field gel electrophoresis by digestion of human DNA of patients with SfiI and hybridization with either probe VAW412 or probe EW401 or their derivatives) to about the total number of the successive nucleotides of the above-defined junction fragment, with said contact being carried out under conditions enabling the production of hybridization complexes formed between said probe and said DNA detecting the above hybridization complexes which have possibly been formed.

The invention yet further relates to a process for the in vitro diagnosis of patients, particularly CMT1 patients (as well as patients manifesting symptoms of CMT1 disease), presenting an alteration on their chromosome 17p, which can be correlated with the fact that they manifest the symptoms of CMT1a disease or that they could develop the symptoms of said disease, which comprises the detection of a duplication of a part of chromosome 17p, simultaneously in either one of the three loci D17S122, D17S125, D17S61, or in two of them, or in all three, preferably by bringing into contact DNA (isolated from a biological sample taken from a patient) with a probe, with said probe containing a sequence constituted of from about 15 successive nucleotides of the VAW409 sequence or its derivatives to about the total number of the successive nucleotides of the VAW409 sequence or its derivatives, with said probe containing a sequence constituted of from about 15 successive nucleotides of the EW401 sequence or its derivatives to about the total number of the successive nucleotides of the EW401 sequence or its derivatives, with said probe containing a sequence constituted of from about 15 successive nucleotides of the VAW412 sequence or its derivatives to about the total number of the successive nucleotides of the VAW412 sequence or its derivatives, with said probe containing a sequence constituted of from about 15 successive nucleotides of any sequence of NotI fragment which comprises the following sequences: pVAW409R1, pVAW409R3, EW401 and VAW412 (with said NotI fragment having $1.2 \times 10^6$ base pairs and being obtainable, preferably obtained, after digesting human DNA with NotI, separating the fragments resulting from digestion, preferably by pulsed field gel electrophoresis, and hybridizing with any of the probers VAW409, EW401 or VAW412 or their derivatives), to about the total number of the successive nucleotides of any NotI fragment such as defined above, with said probe containing a sequence constituted of from about 15 successive nucleotides of the junction fragment of 500 kb (obtainable, preferably obtained, with pulsed field gel electrophoresis by digestion of human DNA of patients with SacII, AscI or FspI and hybridization with probe VAW409 or its derivatives) to about the total number of the successive nucleotides of the above-defined junction fragment, or with said probe containing a sequence constituted of from about 15 successive nucleotides of junction fragment of 600 kb (obtainable, preferably obtained, with pulsed field gel electrophoresis by digestion of human DNA of patients with SfiI and hybridization with either probe VAW412 or probe EW401 or their derivatives) to about the total number of the successive nucleotides of the above-defined junction fragment, with said contact being carried out under conditions enabling the production of hybridization complexes formed between said probe and said DNA detecting the above hybridization complexes which have possibly been formed.

As the probes VAW409, VAW412 and EW401 are contained within the NotI fragment of $1.2 \times 10^6$ base pairs, obtained after digestion human DNA of patients with NotI and separating the resulting fragments by pulsed field gel electrophoresis and hybridizing with any of the probes VAW409, VAW412 or EW401, or their derivatives, any sequence located between VAW409, EW401 and VAW412 sequences can be used as probes.

It has been unexpectedly discovered that, in most CMT1 families tested so far, a duplication simultaneously in the three loci D17S122, D17S125, D17S61 can be detected with probes derived from sequences VAW409, VAW412, EW401, in the CMT1 patients. As observed and described hereafter, in some families, the duplication arises at the same time as the disease (family G, FIG. 3) and is furthermore transmitted together with the disease, indicating that the duplication itself is the primary mutation for CMT1. In some CMT1 families, the duplication originated from an unequal crossing-over event which occurred between two homologous chromosomes at meiosis.

A duplication in only one or two of these loci can also be found.

The locus D17S122 is represented by probe VAW409 and its derivatives: pVAW409R3, pVAW409R3a, pVAW409R3b, pVAW409R1a, pVAW409R1b and pVAW409R1c.

The locus D17S125 is represented by probes VAW412 and its derivatives: pVAW412R3, pVAW412R3a, pVAW412R3b and pVAW412R3c.

The locus D17S61 is represented by probes EW401 and its derivatives: pEW401a, pEW401b, pEW401c and pEW401d.

The duplication can be from about $0.9 \times 10^6$ base. pairs to about $2.2 \times 10^6$ base pairs.

This region contains the gene, or part of it, responsible for CMT1.

The CMT1 gene can be cloned using different approaches, and the corresponding cDNA can be used to detect the duplication in CMT1 patients.

As discussed below, the hybridization of this invention can be carried out in a conventional manner (e.g., using dot-blot or in situ hybridization), if need be, by appropriately adjusting the hybridization conditions and subsequent washing conditions of the hybrids formed.

The probes used in the process of the invention can be formed by cloning of recombinant plasmids containing inserts including the corresponding nucleotide sequences, if need be, by cleaving the latter out from the cloned plasmids upon using the appropriate nucleases and recovering them (e.g., by fractionation according to molecular weight).

The probes according to the invention can also be synthesized chemically, for instance, by the conventional phospho-triester method.

By way of example, hybridization conditions can be the following:

hybridization temperature: 65° C., wash temperature: 65° C., hybridization medium: 0.05 N $Na_2HPO_4/NaH_2PO_4$, pH 7.4; 1 mM EDTA; 7% SDS, wash medium: 0.1×SSC+0.1% SDS up to 2×SSC+0.1% SDS.

It should be emphasized that the indicated temperatures are valid only under the conditions mentioned above. Other hybridization or wash media can be used as well. However, when modifications are introduced, be it either in the probes or in the media, the temperatures at which the probes can be used to obtain the required specificity, should be changed according to known relationships, such as those described in the following reference: B. D. Hames and S. J. Higgins (eds.). Nucleic acid hybridization. A practical approach, IRL Press, Oxford, U.K., 1985.

The hybridization temperature need not necessarily be adjusted to the value at which hybridization is specific and in particular can be lower than the temperature at which hybridization is specific, provided washing is carried out at a temperature corresponding to the value at which hybridization is specific.

The invention relates to a process wherein the duplication is detected:

by screening more than two allelic DNA fragments hybridized with any probe according to the invention, with said fragments resulting from the electrophoresis of human DNA digested by restriction enzymes, or by screening the intensity of fragments of DNA hybridized with any probe according to the invention, with said fragments resulting from the electrophoresis of human DNA digested by restriction enzymes, or by screening supplementary fragments with respect to non-patient fragments, with said supplementary fragments being hybridized with any probe according to the invention, and resulting from the pulsed field gel electrophoresis of human DNA digested by restriction enzymes, or by screening junction fragments hybridized with any probe according to the invention and resulting from the pulsed field gel electrophoresis of human DNA digested by restriction enzymes.

The duplication can be screened by detecting more than two allelic fragments. "More than two allelic fragments" can mean three allelic fragments, which implies that there is a duplication of a fragment of one of the two strands of the chromosome. It can also mean four fragments, if a fragment on one strand and its corresponding fragment on the other strand have been duplicated.

The duplication can be evidenced by the change in intensity. For instance, in a patient heterozygous for the polymorphism, one of the two allelic fragments is duplicated, resulting in an intensity corresponding to about twice the intensity of the same fragment of a non-patient heterozygous for the polymorphism, and in a patient homozygous for the polymorphism, the same allelic fragment is obtained three times, resulting in an intensity of 3/2 as compared with the intensity of the same fragment in a non-patient homozygous for the polymorphism.

Junction fragments are fragments comprising a part of the duplicated sequence defined above and a part of a non-duplicated sequence.

The invention relates to a process wherein the duplication is detected by the screening of three allelic fragments resulting from the digestion of human DNA by a polymorphic restriction enzyme which gives rise to three allelic fragments.

The invention also relates to a process wherein the duplication is detected by the screening of two allelic fragments, with one of them having an intensity corresponding to about twice the intensity with respect to the other allelic fragment, with said two allelic fragments resulting from the digestion of human DNA by a polymorphic restriction enzyme which gives rise to two allelic fragments.

The invention also relates to a process wherein the duplication is detected by the screening of constant fragments, obtained by digestion of human DNA by restriction enzymes, with said fragments having:

an intensity corresponding to about 1.5 times the intensity obtained for the same fragments in a non-patient.

In a preferred embodiment of the process of the invention, the probes are chosen among:

pVAW409R1 deposited under No. 61474 at the ATCC (in glycerol stock) or under No. 61475 (in plasmid DNA) or pVAW409R3 deposited under No. 61476 (in glycerol stock) at the ATCC or under No. 61477 (in plasmid DNA) at the ATCC, pVAW412R3 deposited under No. 61482 at the ATCC (in glycerol stock) or under No. 61483 at the ATCC (in plasmid DNA), EW401 deposited under No. 61464 at the ATCC (in glycerol stock) or under No. 61465 (in plasmid DNA).

Probe pVAW409R3 detects a three allelic MspI polymorphism and contains an EcoRI-EcoRI insert of 2 kb (Wright E. C. et al., 1990, "A genetic map of human chromosome 17p", Genomics 72:103–109).

Probe pVAW409R1 detects a separate two allelic polymorphism and contains an EcoRI-EcoRI insert of 11 kb.

Both MspI polymorphisms, however, are very much obscured by repetitive sequences giving rise to high backgrounds on Southern blots. To avoid these problems, probes pVAW409R1 and pVAW409R3 can respectively be digested with a number of restriction enzymes and searched for DNA fragments free of repetitive sequences. The results of these digests can be seen in the following table:

| For pVAW409R3 (2000 bp): | |
| --- | --- |
| EcoRI - | 2000 bp insert, repetitive |
| EcoRI/BamHI - | 1400 bp "single copy" fragment |
| | 600 bp repetitive |
| EcoRI/HincII - | 1320 bp "single copy" fragment |
| | 680 bp repetitive |
| EcoRI/HindIII - | 2000 bp insert, no HindIII cuts |
| EcoRI/BglI - | 2000 bp insert, no BglI cuts |
| EcoRI/BglII - | 2000 bp insert, no BglII cuts |
| EcoRI/PstI - | 1400 bp repetitive |
| | 600 bp "single copy" fragment |

On the basis of these digests a simple restriction map could be constructed:

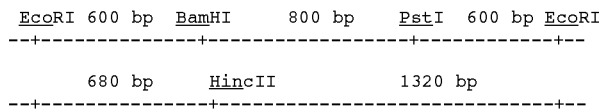

For screening and sequencing purposes five new subclones were made with the following designations:

| Probe | Enzyme | Length |
|---|---|---|
| pVAW409R3 | EcoRI-EcoRI | 2000 bp original probe |
| pVAW409R3a | EcoRI-BamHI | 1400 bp |
| pVAW409R3b | EcoRI-BamHI | 600 bp |
| pVAW409R3c | BamHI-PstI | 800 bp |
| pVAW409R3d | EcoRI-PstI | 1400 bp |
| pVAW409R3e | EcoRI-PstI | 600 bp |

The total sequence of pVAW409R3 has been determined and is given in FIG. 1 (SEQ ID NO:1). The total length of the sequence is 2133 bp.

Probe pVAW409R3a is defined from nucleotide 540 to nucleotide 2133 of FIG. 1 (SEQ ID NO:1).

Probe pVAW409R3b is defined from nucleotide 1 to nucleotide 540 of FIG. 1 (SEQ ID NO:1).

Probes pVAW409R3, pVAW409R3a and pVAW409R3b detect the same polymorphism with MspI.

In all subsequent analysis on MspI Southern blots, probe pVAW409R3a is used because it clearly detects the three allelic MspI polymorphism with very low backgrounds.

According to an advantageous embodiment of the invention, the probes pVAW409R3, pVAW409R3a or pVAW409R3b, preferably pVAW409R3a enable:

detection of three allelic fragments obtained with the MspI restriction enzyme which gives rises to three allelic fragments respectively of 2.9 kb, 2.8 kb and 1.9 kb, or detection of a combination of two allelic fragments chosen among 2.9 kb, 2.8 kb and 1.9 kb, with one of the allelic fragments having an intensity corresponding to about twice the intensity with respect to the other allelic fragment, or detection of one allelic fragment chosen from among 2.9 kb, 2.8 kb and 1.9 kb, with said allelic fragment having:

an intensity corresponding to about three times the intensity obtained for the same fragments in a heterozygous non-patient, or an intensity corresponding to about 1.5 times the intensity obtained for the same fragment in a homozygous non-patient.

To obtain clearer hybridization results on Southern blots with probe pVAW409R1, a similar approach has been followed. Digests with a number of restriction enzymes reveal the following fragments:

| | |
|---|---|
| EcoRI - | 11 kb insert, repetitive |
| EcoRI/BamHI - | 2500 + 2000 bp "single copy" fragments |
| | 200 + 6300 bp repetitive |
| EcoRI/HincII - | 200 + 8000 bp repetitive fragments |
| | 2800 bp "single copy" |
| EcoRI/HindIII - | 1500 + 9000 bp repetitive fragments |
| EcoRI/BglI - | 2500 + 8500 bp repetitive fragments |
| EcoRI/BglII - | 11 kb insert, BglII no cuts |
| EcoRI/PstI - | 2600 + 1000 + 400 bp "single copy" fragments |
| | 3000 + 2000 bp repetitive fragments |

The following three fragments were used in subsequent hybridizations on Southern blots:

| Probe | Enzyme | Length |
|---|---|---|
| pVAW409R1a | BamHI-BamHI | 2000 bp |
| pVAW409R1b | BamHI-EcoRI | 2500 bp |
| pVAW409R1c | BamHI-BamHI | 6500 bp | pVAW409R1a is a 2000 bp BamHI-BamHI subclone from pVAW409R1 ligated in pUC18. It does not detect the MspI polymorphisms but only constant fragments on MspI blots.

pVAW409R1b is a 2500 bp BamHI-EcoRI subclone from pVAW409R1 ligated in pUC18. It detects the MspI polymorphisms, the three allelic polymorphism also detected by pVAW409R3, and the two-allelic polymorphism exclusively detected by pVAW409R1.

pVAW409R1c is a 6500 bp BamHI-BamHI subclone (not single copy) from pVAW409R1 ligated in pUC18. It detects the two-allelic MspI polymorphisms, with fragments of 5.3 kb and 2.7+2.6 kb. The duplication can be detected by density screening of heterozygous patients or homozygous patients (see above).

According to an advantageous embodiment of the invention the probe used is pVAW409R1 or pVAW409R1b, preferably pVAW409R1b, which enables:

detection of three allelic fragments obtained with the MspI restriction enzyme which gives rise to three allelic fragments, respectively, of 2.9 kb, 2.8 kb and 1.9 kb, or detection of a combination of two allelic fragments chosen among 2.9 kb, 2.8 kb and 1.9 kb, with one of the allelic fragments having an intensity corresponding to about twice the intensity of the other allelic fragment, or detection of one allelic fragment chosen from among 2.9 kb, 2.8 kb and 1.9 kb, with said allelic fragment having:

an intensity corresponding to about three times the intensity obtained for the same fragments in a heterozygous non-patient, or an intensity corresponding to about 1.5 times the intensity obtained for the same fragment in a homozygous non-patient, and detection of a MspI polymorphism of two different allelic fragments of 5.3 kb and 2.7 kb, one of them having an intensity corresponding to about twice the intensity with respect to the other one, or detection of one allelic fragment of these two allelic fragments, with said allelic fragment which is detected having:

an intensity corresponding to about three times the intensity obtained for the same fragments in a heterozygous non-patient, or an intensity corresponding to about 1.5 times the intensity obtained for the same fragment in a homozygous non-patient.

According to another embodiment of the invention, the probe used is pVAW409R1a which enables detection of constant fragments with MspI, having:

an intensity corresponding to about 1.5 times this intensity obtained for the same fragments in a non-patient.

According to another embodiment of the invention, the probe used is pVAW409R1c which enables detection of a MspI polymorphism of two different allelic fragments of 5.3 kb and 2.7 kb, with one of them having an intensity corresponding to twice the intensity with respect to the other one, or detection of one allelic fragment of these two allelic fragments, with said allelic fragment which is detected having:
an intensity corresponding to about three times the intensity obtained for the same fragments in a heterozygous non-patient, or
an intensity corresponding to about 1.5 times the intensity obtained for the same fragment in a homozygous non-patient.

According to another advantageous embodiment of the invention, the probe used is VAW409, pVAW409R1a, pVAW409R1b, pVAW409R1c, pVAW409R3a or pVAW409R3b, which enables detection by pulsed field gel electrophoresis of a fragment of about 500 kb hybridized with any of the above-mentioned probes, with the fragment being obtained after digestion with SacII, AscI or FspI of human DNA of patients, particularly CMT1 patients, and with the fragment being supplementary with respect to the fragments obtained with non-patient human DNA digested with SacII, AscI or FspI.

pVAW412R3 insert 3.8 kb, is a subclone from a phage VAW412.

Three subfragments were used, the subfragments were obtained by cutting the subclone pVAW412R3 simultaneously by the enzymes EcoRI and BqlI. Three insert derived fragments are obtained after gel electrophoresis:

pVAW412R3a is a 2400 bp fragment which is a single copy fragment and detects the first MspI polymorphism with bands of 10.5 and 5.4 kb;

pVAW412R3b is a 1400 bp fragments which is a single copy and which (presumably) detects the second MspI polymorphism with bands of 2.6 and 1.9+0.7 kb;

pVAW412R3c is a fragment of 300 bp which is repetitive.

The EW401 has an insert of 4500 bp.

Four fragments were obtained by digesting the clone EW401 with the enzymes EcoRI and HincII. The four insert derived fragments are obtained after agarose gel electrophoresis:

pEW401a is a 1800 bp single copy fragment which recognizes a MspI polymorphism with fragments of 5.5 and 4.4 kb, pEW401b is a 1500 bp repetitive fragment, which presumably recognizes a MspI polymorphism with fragments of 5.5 and 4.4 kb, pEW401c is a 900 bp single copy fragment which recognizes a MspI polymorphism with fragments of 5.5 and 4.4 kb, pEW401d is a 300 bp single copy fragment which recognizes a MspI polymorphism with fragments of 5.5 and 4.4 kb.

According to a preferred embodiment of the invention, the probe used is EW401, pEW401a, pEW401b, pEW401c or pEW401d, preferably pEW401a which enables:

detection of two allelic fragments obtained with the MspI restriction enzyme which gives rises to two allelic fragments respectively of 5.5 kb and 4.4 kb, with one of the allelic fragments having an intensity corresponding to twice that of the other allelic fragments, or detection of one allelic fragment chosen from among 5.5 kb and 4.4 kb, with said allelic fragment having:
an intensity corresponding to about three times the intensity obtained for the same fragments in a heterozygous non-patient, or
an intensity corresponding to about 1.5 times the intensity obtained for the same fragment in a homozygous non-patient.

According to a preferred embodiment of the invention, the probe used is pVAW412R3 which enables simultaneously detection of two diallelic polymorphisms obtained with a MspI restriction enzyme corresponding respectively to fragments of 10.5 kb and 5.4 kb and to fragments of 2.6 kb and 1.9+0.7 kb.

According to another preferred embodiment of the invention, the probe used is pVAW412R3a which enables detection of a MspI polymorphism of two different allelic fragments of 10.5 kb and 5.4 kb, with one of them having an intensity corresponding to twice the intensity with respect to the other one, or detection of one allelic fragment chosen from among 10.5 kb and 5.4 kb, with said allelic fragment having:
an intensity corresponding to about three times the intensity obtained for the same fragments in a heterozygous non-patient, or
an intensity corresponding to about 1.5 times the intensity obtained for the same fragment in a homozygous non-patient.

According to another preferred embodiment of the invention, the probe used is pVAW412R3b which enables detection of a MspI polymorphism of two different allelic fragments of 2.6 kb and 1.9+0.7 kb, with one of them having an intensity corresponding to twice the intensity with respect to the other one, or detection of one allelic fragment chosen from among 2.6 kb and 1.9+0.7 kb, with said allelic fragment having:
an intensity corresponding to about three times the intensity obtained for the same fragments in a heterozygous non-patient, or
an intensity corresponding to about 1.5 times the intensity obtained for the same fragment in a homozygous non-patient.

According to another advantageous embodiment of the invention, the probe used is VAW412, pVAW412R3, pVAW412R3b, pVAW412R3c, EW401, pEW401a, pEW401b, pEW401c or pEW401d, which enables detection by pulsed field gel electrophoresis of a fragment of about 600 kb hybridized with any of the above-mentioned probes, with the fragment being obtained after digestion with SfiI of human DNA of patients, particularly CMT1 patients, and with the fragment being supplementary with respect to the fragments obtained with human DNA of non-patients digested with SfiI.

According to another embodiment of the invention, the process for the in vitro diagnosis of patients, particularly CMT1 patients (as well as patients manifesting symptoms of CMT1 disease), presenting an alteration on their chromosome 17p which can be correlated with the fact that they manifest the symptoms of CMT1a disease or that they could develop the symptoms, comprises:

the possible previous amplification of the amount of a fragment of the duplication of a part of chromosome 17p, with said fragment being liable to be contained in a biological sample taken from said patient by means of a DNA primer set, contacting the above-mentioned biological sample with any one of the probes defined above, under conditions enabling the production of an hybridization complex formed between said probe and said nucleotide sequence, detecting in patients the above-mentioned hybridization complex which has been possibly formed and the intensity obtained with the hybridization complex should correspond to 1.5 times to the intensity obtained in non-patients.

The invention also relates to a kit for the in vitro diagnosis of patients, particularly CMT1 patients (as well as patients manifesting symptoms of CMT1 disease), presenting an alteration on their chromosome 17p, which can be correlated with the fact that they manifest the symptoms of CMT1a disease or that they could develop the symptoms of said disease, which comprises:

a determined amount of a nucleotide probe according to the invention, possibly primers to amplify a fragment of the duplication of a part of chromosome 17p, advantageously the appropriate medium for creating an hybridization reaction between the fragments to be detected and the above-mentioned probe, advantageously, reagents enabling the detection of the hybridization complexes which have been formed between the fragments and the probe during the hybridization reaction.

The invention also relates to a process for the in vitro diagnosis of patients, particularly CMT1 patients, (as well as patients manifesting symptoms of CMT1 disease), presenting an alteration on their chromosome 17p which can be correlated with the fact that they manifest the symptoms of CMT1a disease or that they could develop the symptoms, comprising the steps of:

amplifying a fragment of a duplicated part of chromosome 17p, which fragment may be contained in a biological sample taken from such patients, by means of a DNA primer set such as:

right primer:
5' CAT ACA ATG CAC GCA GTT GA 3' (SEQ ID NO:2) bp-position 601,
left primer:
5' AAA CCC AGA ACT TCC ACT TC 3' (SEQ ID NO:3) bp-position 875, or
right primer:
5' CAT ACA ATG CAC GCA GTT GA 3' (SEQ ID NO:2) bp-position 601,
left primer:
5' TTG GTA CAA CCT TCC TGG AG 3' (SEQ ID NO:4) bp-position 940, amplifying a sequence outside the duplication of a part of chromosome 17p, contained in a biological sample taken from such patients, by means of a DNA primer set such as:

right primer:
5' CAA ATC CTG CCC ATG AAG TT 3' (SEQ ID NO:5) bp position 9,
left primer:
5' ATG TAT TGG GCT GGT TAC TG 3' (SEQ ID NO:6) bp-position 199, or
right primer:
5' ATC CAT TCA TCC ATT CTC CC 3' (SEQ ID NO:7),
left primer:
5' CAA CAT CAG GTC AAC CAG AG 3' (SEQ ID NO:8), and comparing the amount of the amplified fragment of the duplication of a part of chromosome 17p and the amount of the amplified sequence outside the duplication, which is in the ratio of 3/2 if the patients suffer from an alteration of chromosome 17p.

A set of primers respectively for the duplicated part and a non-duplicated part can be as follows (PCR1);

the primers for the duplicated region can be sequences from pVAW409R3 such as:
right primer:
5' CAT ACA ATG CAC GCAGTT GA 3' (SEQ ID NO:2) bp-position 601
left primer:
5' AAA CCC AGA ACT TCC ACT TC 3' (SEQ ID NO:3) bp-position 875;
the PCR amplification results in a DNA fragment of 274 bp;
the primers for the single copy reference DNA fragment can be taken from the reference DNA which is P1041, a non-duplicated region of 17p; with said primers being:
right primer:
5' CAA ATC CTG CCC ATG AAG TT 3' (SEQ ID NO:5) bp position 9,
left primer:
5' ATG TAT TGG GCT GGT TAC TG 3' (SEQ ID NO:5) bp-position 199;
the PCR amplification results in a DNA fragment of 190 bp.

Another set of primers respectively for the duplicated part and for a non-duplicated part can be as follows (PCR2):

the primers for the duplicated region can be sequences from pVAW409R3 such as:
right primer:
5' CAT ACA ATG CAC GCA GTT GA 3' (SEQ ID NO:2) bp-position 601,
left primer:
5' TTG GTA CAA CCT TCC TGG AG 3' (SEQ ID NO:4) bp-position 940;
the PCR amplification results in a DNA fragment of 339 bp;
the primers for the single copy reference DNA fragment can be the primers for D21S13 locus as published by Stinissen et al. (1990) Nucl. Acids Res. 18:3672, with said primers being:
right primer:
5' ATC CAT TCA TCC ATT CTC CC 3' (SEQ ID NO:7),
left primer:
5' CAA CAT CAG GTC AAC CAG AG 3' (SEQ ID NO:8);
the PCR amplification results in a fragment of 460 bp.

PCR reactions are performed in a total volume of 50 µl comprising 0.1 to 0.2 µg genomic DNA, 1.5 mM MgCl$_2$, 0.05 mM KCl, 10 mM Tris pH 8.3, 0.001% (w/v) gelatine, 0.2 mM nucleotide triphosphates, 50 pmol of each of the 4 primers and 2 U Taq DNA polymerase (BRL, Bethesda, USA). The samples are covered with 50 µl mineral oil and 35 three step cycles (1.30 min. 94° C.; 1.30 min. 66° C. for PCR 1 and 1.30 min. 60° C. for PCR 2, respectively, 2 min. 72° C.) are performed in a Cetus Thermocycler apparatus. The PCR products are separated on a 3% standard agarose gel (2.5% Nusieve and 0.5% seakem (FMC, Maine, USA) at 2.5 V/cm for 5 hours. The UV-transilluminated gels are photographed with a Polaroid 665 film and the density of the DNA fragments is analyzed on a densitometer using the negative of the photograph. Alternatively, one primer of the reference DNA and one primer of the target DNA is radioactively labeled (Dracopoli and Meisler Genomics 7:97–102 (1990) using [gamma $^{32}$P-dATP]. After PCR amplification and separation on an agarose gel, an autoradiograph is made and analyzed on the densitometer.

The invention also relates to a kit for the in vitro diagnosis of patients presenting an alteration on their chromosome 17p, which can be correlated with the fact that they manifest the symptoms of CMT1a disease or that they could develop the symptoms of said disease, which comprises:

primers to amplify a fragment of the duplication of a part of chromosome 17p, with said fragment being liable to be contained in a biological sample taken from said patient, primers to amplify a sequence outside the duplication of a part of chromosome 17p, contained in a biological sample taken from a patient.

The probes, the process and the kits of the invention are advantageously used on biological samples taken from patients, with such biological samples containing DNA and being advantageously constituted by blood samples.

The invention further relates to a method for producing a transgenic non-human mammalian animal, such as a mouse, rat, dog, guinea pig or monkey, particularly a mouse, having a probability of developing symptoms of CMT1a disease. The method comprises the step of incorporating one or more genes encoding a peripheral myelin protein 22 (PMP-22) into the genome of the non-human mammalian animal, whereby the animal overproduces the PMP-22 protein. The transgenic animal, transformed with at least one PMP-22 gene, can be produced in a now well known manner, for example, according to the protocol described in International Review of Cytology, vol. 115, p. 171–222 (1989), as well as by the method generally described in European patent application 85304490. The selection of the specific PMP-22 gene, used for transforming a particular animal, is not believed to be critical, and the gene can be foreign or endogenous to the animal but is preferably endogenous. In this regard, the PMP-22 gene in trembler (Tr) mouse, which is localized on mouse chromosome 11 (Suter et al (1992) Nature 356:241) and which shows a high degree of sequence homology to the mouse chromosome 11 growth arrest specific 3 (GAS-3) gene (Manfioletti et al (1990) Mol. Cell Biol. 10: 2924), can be used, particularly for transforming mice. Suitable PMP-22 genes in other mammals can be identified, isolated and sequenced in a conventional manner using the mouse PMP-22/GAS-3 gene as a probe, such as the 1.8 kb cDNA CD25 isolated from a rat sciatic nerve cDNA library (Spreyer et al (1991) EMBO J. 10:3661). In this regard, using the rat PMP-22/GAS-3 cDNA cD25 as a probe, the human PMP-22/GAS-3 gene has been found to have a size of no more than about 100 kb, and the gene has been localized to human chomosome region 17p11.2 and has been found to be present, in duplicate, within the CMT1a duplication in chromosome 17p of this invention and not to be interrupted by the duplication. In fact, each copy of the human PMP-22/GAS-3 gene is within 50 to 100 kb telomeric to VAW409 of this invention and at least 500 kb from the duplication junction site.

The invention further relates to a process and kit, as described above, for in vitro diagnosis of an alteration of a patient's chromosome 17p, correlated with CMT1a disease, which process and kit further comprise the use of a probe for a PMP-22 gene, particularly a PMP-22/GAS-3 gene, of the patient in order to detect the presence of any duplication of the patient's PMP-22 gene, particularly PMP-22/GAS-3 gene, within the above-described duplication of part of the 17p chromosome. Such a probe can comprise a PMP-22 gene, particularly a PMP-22/GAS-3 gene, or a portion thereof which comes from any mammal, as described above, but which preferably comes from a human and which will suitably hybridize under conventional diagnosis laboratory conditions to any duplicate PMP-22 genes of the patient.

CONDITIONS OF THE USE OF PROBES

The probes of the invention are advantageously labeled. Any conventional label can be used. The probes can be labeled by means of radioactive tracers such as $^{32}P$, $^{35}S$, $^{125}I$, $^{3}H$ and $^{14}C$.

The radioactive labeling can be carried out according to any conventional method such as terminal labeling at the 3' or 5' position with the use of a radiolabeled nucleotide, a polynucleotide kinase (with or without dephosphorylation by a phosphatase) or a ligase (according to the extremity to be labeled). One of the probes of the invention can be the matrix for the synthesis of a chain consisting of several radioactive nucleotides or of several radioactive and nonradioactive nucleotides. The probes of the invention can also be prepared by a chemical synthesis using one or several radioactive nucleotides. Another method for radioactive labeling is a chemical iodination of the probes of the invention which leads to the binding of several $^{125}I$ atoms on the probes.

If one of the probes of the invention is made radioactive to be used for hybridization with a nonradioactive DNA, the method of detecting hybridization will depend on the radioactive tracer used. Generally, autoradiography, liquid scintillation, gamma counting or any other conventional method enabling one to detect an ionizing ray issued by the radioactive tracer can be used.

Nonradioactive labeling can also be used by associating the probes of the invention with residues having: immunological properties (e.g. antigen or hapten), a specific affinity for some reagents (e.g. ligand), properties providing a detectable enzymatic reaction (e.g. enzyme, co-enzyme, enzyme substrate or substrate taking part in an enzymatic reaction), or physical properties such as fluorescence or emission or absorption of light at any wavelength. Antibodies which specifically detect the hybrids formed by the probe and the target can also be used.

A nonradioactive label can be provided when chemically synthesizing a probe of the invention, the adenosine, guanosine, cytidine, thymidine and uracyl residues thereof being liable to be coupled to other chemical residues enabling the detection of the probe or the hybrids formed between the probe and a complementary DNA fragment. However, the nucleotide sequence of the probe when modified by coupling one or more nucleotides to other chemical residues would be the same as the nucleotidic sequence of one of the probes of the invention.

The invention also relates to processes for detecting DNA by hybridization with the probes of this invention, which have been labeled and can be detected as described above. In this regard, conventional methods of hybridization can be used.

For detecting the duplication, genomic DNA can be prepared as explained in the examples and contacted with one or several probes of the invention. This contact can be carried out on an appropriate support such as a nitrocellulose, cellulose, or nylon filter in a liquid medium or in solution. This contact can take place under sub-optimal, optimal conditions or under restrictive conditions (i.e., conditions enabling hybrid formation only if the sequences are perfectly homologous on a length of molecule). Such conditions include temperature, concentration of reactants, the presence of substances lowering the optimal temperature of nucleic acid pairing (e.g., formamide, dimethylsulfoxide and urea) and the presence of substances apparently lowering the reaction volume and/or accelerating hybrid formation (e.g., dextran sulfate, polyethylene glycol or phenol).

The elimination of probe of the invention which has not hybridized can be carried out by washing with a buffer solution of appropriate ionic strength and at an appropriate temperature, with or without treatment with S1 nuclease or any other enzyme digesting single-strand DNA but not digesting double-strand DNA.

In a liquid medium, the hybrids of the probes of the invention paired to the cellular DNA fragments can be separated from the rest of the liquid medium in different ways (e.g., by chromatography over hydroxyapatite).

Then the hybridized probes are detected by means of the label on the probe.

In order to target the duplication of fragments of the chromosome 17p from which the labeled probes of the invention derive, after treating DNA by one or several enzymes and denaturation of DNA fragments (i.e., separation of both chains), one of the probes of the invention is contacted with the DNA fragments under conditions enabling hybridization, and after the time necessary to complete the hybridization, the non-hybridized fragments are separated from the hybridized fragments and the label is detected according to classical methods.

Generally speaking, the different probes of the invention can also be contained in recombinant DNA enabling their cloning, if the presence of a heterologous DNA is not a hindrance for the specificity of the probes in the encompassed uses.

DESCRIPTION OF THE FIGURES

FIG. 1 represents the nucleotide sequence of pVAW409R3 (SEQ ID NO:1).

Lanes 1, 4 and 11 correspond to non-CMT1 patients.

Lanes 2, 3 and 5 to 10 correspond to CMT1 patients from different families.

Non-CMT1 patients show bands of 500 kb (B) and 550 kb (A). All tested CMT1 patients have an extra band of 450 kb (C) which is a junction fragment.

In addition to the density screening on MspI Southern blots, this method is interesting for the screening of the CMT patients as it detects the presence of a structural alteration with greater reliability the presence of a structural alteration.

Figure 6:
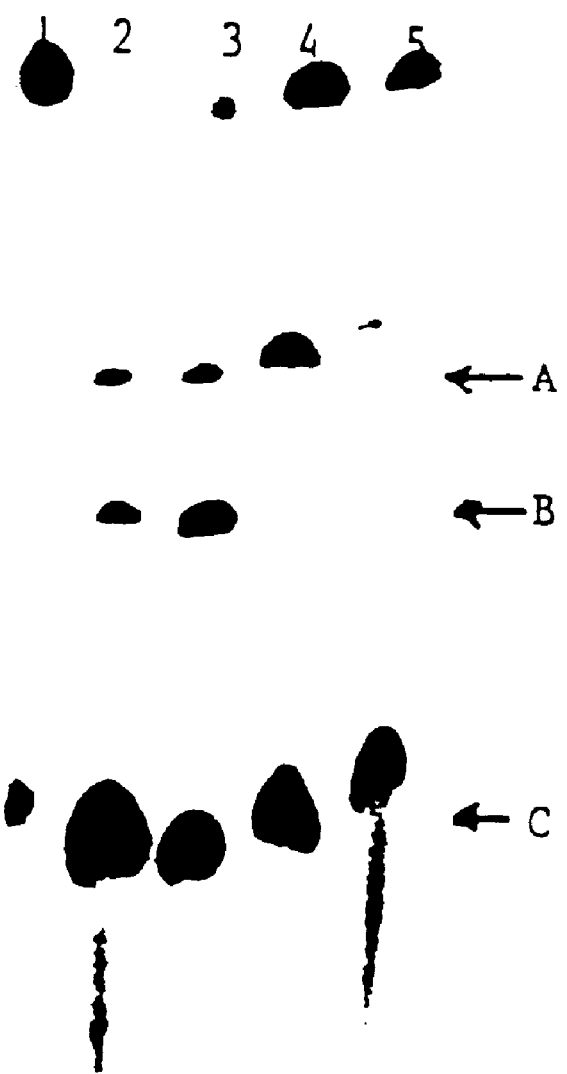

FIG. 6 represents a pulsed field gel electrophoresis of SfiI digested DNA from CMT1 patients and non-patients. DNA was digested, electrophoresed and blotted onto Hybond N+ (Amersham) as described in the text. The filter was hybridized with probe pVAW412R3a, but the same hybridization signals were obtained with any derivative probe of pVAW412R3 and pEW401.

Lanes 1, 4 and 5 correspond to non-CMT1 patients.

Lanes 2 and 3 correspond CMT1 patients from different families.

Non-CMT1 patients show bands of 300 kb (C) and 800 kb (A). All tested CMT1 patients have an extra band of 600 kb (B) which is a junction band.

EXAMPLES

PROCEDURE FOR GENOMIC DNA ISOLATION FROM HEPARINIZED BLOOD SAMPLES

DNA from CMT patients and related individuals can be isolated from 10 ml total blood samples containing Li-heparin or $Na_2EDTA$ as anticoagulant. Erythrocytes are lysed by adding three volumes cold hemolysis solution (155 mM $NH_4Cl$, 10 mM $KHCO_3$ and 1 mM $Na_2EDTA$, pH 7.4, stored at 4° C.) to 10 ml total blood. Incubation is carried out on crushed ice during 20 minutes and the lymphocytes are centrifuged at 900 g for 10 minutes at 4° C. The supernatant is removed and the lymphocyte pellet is washed in 10 ml hemolysis solution. Centrifugation is repeated and the pellet is resuspended in two volumes (20 ml) SE lysis buffer (75 mM NaCl, 24 mM $Na_2EDTA$, pH 8.0) at room temperature. 200 µg/ml pronase are added (EC 3.4.24.4. 1 g pronase is dissolved (Boehringer) in 50 ml $H_2O$ during 2 hours at 37° C. for autodigestion) and the suspension is adjusted to 1% (v/v) of sodium-dodecylsulphate (SDS). Incubation is carried out during one day at 30° C. to allow lysis of the lymphocytes.

The DNA is extracted from the lysis suspension with an equal volume of 25/24/1 (v/v/v) phenol-chloroform-isoamyl alcohol (500 g phenol are dissolved in 50 ml 10 mM Tris.HCl, pH 7.5 overnight, an equal volume of 24/1 (v/v) chloroform-isoamyl alcohol and 0.1% 8-hydroxy-quinoline are added) during 30 minutes in a top-over-top rotator and centrifugation is carried out at 2520 g, during 20 minutes. The aqueous phase is transferred to a fresh tube by pipeting with Pasteur pipets. Extraction is carried out a second time with an equal volume of chloroform-isoamyl alcohol (24/1). After this extraction, the DNA is precipitated with 1/30 of the volume 3 M sodium acetate, pH 5.5 and two volumes isopropanol. The tube is gently turned until the DNA precipitates into a small flock. The precipitate is washed in 70% ethanol and air dried. The flock is dissolved in approximately 500 µl $1 \times TE^{-4}$ (10 mM Tris.HCl, 0.1 mM $Na_2EDTA$, pH 7.5) to a final, concentration of 0.5 µg DNA/µl. One can measure the amount of DNA by spectrophotometry at 260 nm. This protocol is a modification of the method described by Baas F. et al. (1984, "Unusual scarity of restriction site polymorphism in the human thyroglobulin gene. A linkage study suggesting autosomal dominance of defective thyroglobulin allele" Human Genetics 67:301–305) and Maniatis T. et al. (1989, Molecular Cloning: a Laboratory Manual. Second edition, Cold Spring Harbor Laboratory Press).

Isolation Procedure of Genomic Human DNA for the Use in Pulsed Field Gel Electrophoresis (PFGE)

An equal volume of 1×phosphate buffered saline (PBS, Gibco) is added to 10 ml heparinized blood sample, at room temperature with a plastic sterile pipet (10 ml). Fifteen Ficoll Hypaque (marketed by Pharmacia) is then added with a pipet in the bottom of the tube, below the blood level, and air bubbles should not be generated. Centrifugation is carried out for 30 minutes at 400 g. The lymphocytes are recovered carefully from the Ficoll gradient and transferred to a fresh tube with a Pasteur pipet. The lymphocytes are then washed with 45 ml 1×PBS and centrifuged at 400 g for 10 minutes. The supernatant is removed and the cell pellet is resuspended in 45 ml 1×PBS after which centrifugation is again carried out. The lymphocyte pellet is resuspended at a final concentration of $4.2 \times 10^7$ cells/ml 1×PBS.

An equal volume of 1% Low Melting Point agarose (LMT, Bethesda Research Laboratories, England) dissolved in 1×PBS at 50° C. is added to the cells. The cells are divided in 100 µl aliquots into a well-mould. Each mould contains $1.7 \times 10^6$ cells/80 µl or 10 µg human DNA. Twenty cell blocks are removed after coagulation in lysis solution containing 10 ml 0.5 M $Na_2EDTA$, 0.5 ml sarcosyl (20% aqueous solution), 1 ml proteinase K (10 mg/ml aqueous solution, stored at −20° C.) and incubation is carried out at 50° C. for 48 hours. The cell blocks are washed four times with 45 ml 1×TE (10 mM Tris.HCl, 1 mM $Na_2EDTA$, pH 8.0) to remove all lysis solution. Ten ml 1×TE solution, 10 µl PMSF (phenylmethylsulphonyl fluoride, 40 mg/ml ethanol) is finally added and incubation is carried out for 30 minutes at 50° C. with shaking. This procedure is repeated and washing is done with 1×TE. The cell blocks are stored at 4° C. in 45 ml 0.5 M $Na_2EDTA$.

Digestion of Genomic Human DNA with MspI and Southern Blotting

Aliquots of 5 µg high molecular weight DNA from CMT1a patients and relatives are digested overnight at 37° C. to completion with the MspI restriction endonuclease (3 U/µg DNA) according to manufacturer's instructions (BRL) along with 1 µl spermidine (100 mM aqueous solution stored at −20° C.). Simultaneously, a small amount of the individual DNA can be digested in the presence of 0.2 µg lambda phage DNA as a control to the completion of the reaction. The digestion products can be visualized by electrophoresis in a 1×TBE (1×TBE; 0.09 M Tris, 0.09 M $H_3BO_3$, 0.002 M $Na_2EDTA$) 0.7% agarose gel containing 5 µl/100 ml ethidium bromide (10 mg/ml aqueous solution). The reaction is inhibited by adding 1×SLM (Stop and Loading Mixture 10×SLM; 0.125 mM $Na_2EDTA$, 0.5% SDS, 50% sucrose and 0.125% bromophenol blue).

Digested DNA and molecular weight markers are subjected to electrophoresis (14 h, 27 V, 45 mA) in 1×TAE (0.04 M Tris.HCl, 0.04 M sodium acetate, 2 mM $Na_2EDTA$, pH 7.7) buffer containing EtBr, through a 1×TAE stained EtBr horizontal submarine 0.7% agarose (BRL) gel. A picture from the gel containing the separated MspI fragments can be taken as control.

The gel is gently shaken in 0.25 M HCl for depurination during 5 to 10 minutes until the blue SLM tracking dye changes into green. The solution is there removed and the gel is denatured for 2×15 minutes in 0.5 M NaOH, 1.5 M NaCl. The gel is neutralized during 2×15 minutes in 1.5 M NaCl, 0.5 M Tris.HCl, pH 7.2. The DNA is transferred overnight to Hybond N+ (Amersham, England) nylon membranes by Southern blotting in 10×SSC (20×SSC; 3 M NaCl, 0.3 M sodium citrate, pH 7.0). After blotting, the membrane is removed, briefly wetted in 2×SSC, 0.1 M Tris.HCl, pH 7.2 and the DNA is finally fixed by immersion in 0.4 M NaOH for 20 minutes. After immersion the membrane is rinsed in 2×SSC, 0.1 M Tris.HCl, pH 7.2 and dried. If desired the membrane can be cut lengthwise in two pieces for facilitating manipulation during the hybridizations.

Digestion of Genomic DNA with SacII, SfiI and NotI and Fractionation by Pulsed Field Gel Electrophoresis (PFGE)

A 10 µg DNA agarose cell block (stocked in 0.5 M $Na_2EDTA$ at 4° C.) is transferred from each CMT1a patient who is to be examined to a separated fresh tube containing 45 ml 1×TE, pH 8.0. Incubation is carried out for 30 minutes at 50° C. and the solution is removed. This procedure is repeated once and the block is placed in an Eppendorf tube. Twenty µl bovine serum albumine (5 µg BSA/µl aqueous solution, BRL), 20 µl 10×restriction enzyme buffer and 3 U/µg DNA of the enzyme (Biolabs) rare cutter restriction enzyme are added. The final volume is adjusted to 200 µl with sterile $H_2O$. Incubation is carried out overnight at the appropriate temperature for digestion and the reaction is stopped on ice. Yeast chromosomes are used as high molecular weight markers and reference DNA is taken from a healthy person.

For pulsed field gel electrophoresis, the LKB Pulsaphor apparatus (Pharmacia/LKB) was used. The DNA blocks are placed into appropriate wells from a 0.5×TBE 1% Seakem-Agarose (BRL) gel. The wells are sealed with 1% LMT agarose in 0.5×TBE. The electrophoresis is carried out under the following conditions; 0.5×TBE at 12° C., 180 V, 120 mA, 40 h, 60 sec. pulse interval in a hexagonal field. After electrophoresis, the separation is examined with EtBr staining. Depurination, denaturation and neutralization occur as previously described. The DNA is transferred by Southern blotting on Hybond N+ nylon membranes. This protocol is a modification of the method described by Harris P. C. et al. (1990, "A long-range restriction map between the α-globin complex and a marker closely linked to the polycystic kidney disease 1 (PKD1) locus" Genomics 7:195–206).

Isolation of Recombinant Plasmids Containing the Different Probes of the Invention E. coli DH5α (rec⁻) host cells are grown in 100 ml LB broth (1 g bacto-tryptone, 0.5 g bacto-yeast extract, 1 g NaCl), pH 7.5 to a density of 0.25 at $A_{600}$ and centrifuged (900 g, 10 minutes). The pellet is resuspended on ice in 50 mM $CaCl_2$ (1/10 of the growth volume) and 15% (v/v) glycerol and stored in 200 µl aliquots at −70° C.

The competent DH5α host cell aliquots are transformed with 1 to 10 ng of the recombinant plasmid DNA during a 10-minute incubation on crushed ice followed by a heat shock in a 42° C. water bath for 90 seconds. Chilling is carried out by returning the tubes immediately to 0° C. Next, 800 µl of ampicillin (100 µg/ml) containing LB medium are added, and incubation is carried out at 37° C. with moderate agitation for 30–60 minutes. This protocol is a modification of the method of Hanahan D. (1985, Techniques for transformation of E. coli. In DNA cloning Volume 1: A practical Approach. IRL Press, Oxford, Washington D.C. ed. Glover, D. M. p. 109–135) on a selective LB plate (12 g/l agar) and incubated overnight at 37° C.

A single bacterial colony transformed with the recombinant plasmids is inoculated in 5 ml LB medium containing ampicillin (100 µg/ml) and grown overnight while being vigorously shaken at 37° C. Next, 1.5 ml of the culture is poured into an Eppendorf tube. Centrifugation is performed for 1 minute in an Eppendorf centrifuge. The medium is removed by aspiration, leaving the bacterial pellet as dry as possible. The pellet is resuspended by vortexing in 100 µl of an ice-cold solution of 50 mM sucrose, 10 mM $Na_2EDTA$, 20 mM Tris.HCl, pH 8.0, and 4 mg/ml lysozyme. Powdered lysozyme is added to the solution just before use. The mixture is left for 5 minutes at rooK temperature, after which 200 µl of a freshly prepared, ice-cold solution of 0.2 M NaOH and 1% SDS is added. The contents are mixed by inverting the tube rapidly a few times without vortexing. The tube is left on ice for 5 minutes. Then, 150 µl ice-cold 3 M potassium acetate pH 4.8 is added. The tube is inverted a few times rapidly and placed on ice for 10 minutes. Centrifugation is carried out for 5 minutes in an Eppendorf centrifuge and the supernatant containing the plasmid is transferred to a fresh tube. An equal volume of phenol/chloroform/isoamyl alcohol (25/24/1) is added and mixed gently. After centrifuging for two minutes the aqueous supernatant is transferred to a fresh tube. The extraction is repeated with an equal volume chloroform/isoamyl alcohol (24/1). Two volumes 98% ethanol are added to the extracted supernatant and left for 10 minutes on ice. Centrifugation is performed for 5 minutes; the supernatant is removed and the pellet is washed in 1 ml 70% ethanol. After recentrifugation, all of the supernatant is removed and the pellet is air-dried. The pellet is diluted with 25 µl 1×TE⁻⁴ (pH 8.0) containing DNase-free pancreatic RNase (20 µg/ml). The digestion of the bacterial RNA is allowed to proceed for 20 minutes of incubation at 65° C. The plasmid concentration is measured by 1×TBE, 0.7% agarose gel electrophoresis containing EtBr by comparing it with a reference plasmid.

Recovering of Single Copy Fragments of the Probes of the Invention

The total plasmid solution is digested to completion with the appropriate restriction enzymes according to the manufacturer's instructions (BRL). The digested plasmid and markers (pBR322 or pUC8) are subjected to 1×TBE 0.7% agarose gel electrophoresis overnight at 20 V. The single copy fragments are cut off from the gel. The cap of an Eppendorf tube is cut and a small hole is made in the bottom. A little glass-wool (3 mm) is put in the bottom and the gel fragment is placed in this tube. This tube is placed on top of another Eppendorf tube and centrifugation is carried out for 15 minutes at 6000 rpm. The DNA fragments can be recovered from the agarose gel by this method. The DNA concentration is adjusted to 1 ng/µl. The recovered double-stranded linear DNA fragments in 25 µl aliquots (25 ng DNA) are divided in separated Eppendorf tubes.

Labeling Procedure

The probe DNA is labeled by oligo-priming using the Multi-Prime kit of BRL and [α-$^{32}$P]dCTP (3000 Ci/mmol, Amersham). The 25 µl pVAW409R1a or pVAW409R3a DNA fragments are denatured by boiling for 2 minutes and followed by immediate cooling to 37° C. for 10 minutes. In a separate Eppendorf 15 µl of the random primer mixture, 6 µl dATP, dGTP and dTTP, 1 µl Klenow-DNA polymerase, 2 to 3 µl [α-$^{32}$P]dCTP are added. This reaction solution is mixed with the 25 µl denatured DNA fragments to a final volume of 50 µl and the reaction is allowed to continue at room temperature for 3 hours.

Twenty-five µl 25 mM $Na_2EDTA$, 0.1% phenol red and 1% dextran blue are added in order to stop the reaction.

The reaction mixture is then placed on a small (7 ml, Pasteur pipet) gel filtration column (20 g Sephadex G50, Pharmacia, dissolved in 300 ml 1×TE⁻⁴ 10 mM Tris, 0.1 mM EDTA, pH 7.5). The probe (blue fraction) is collected from the reagents and substrates (red fraction) with 1×TE⁻⁴ in an Eppendorf tube and stored on ice. The amount of radioactive incorporation must be at least 10×10⁶ cpm/ml. The labeled DNA is denatured for 10 minutes by boiling, followed by and immediate cooling on ice for 15 minutes.

The Hybond N+ nylon membranes containing the MspI digested human DNA is preincubated in a 65° C. incubator with 20 ml Church buffer (0.5 M $Na_2PO_4$, 1 mM $Na_2EDTA$, 7% SDS and 4 ml 85% $H_3PO_4$, pH 7.2, stored at 30° C.) during 15 minutes in a small appropriate container (Rubbermaid n3419). The air bubbles are removed between the two membranes and the container is closed. The probes are added to the membranes, the container is shaken gently without generating bubbles, and closed. The probe is let to hybridize overnight in a 65° C. incubator.

The hybridization mixture is removed and the membranes are washed twice in 2×SSC+0.1% SDS for 15 minutes at 65° C. The washing is repeated in 1×SSC+0.1% SDS until 5 to 10 cps radioactivity remains on the filters. The hybridized membrane is rinsed in 2×SSC and dried it between Whatman paper. The filter is packed between plastic fall and the membrane is exposed to a Kodak-ortho G radiograph film at −70° C. The film is developed after a few hours to detect the D17S122, D17S125 and D17S61 polymorphisms and the duplication in CMT1 patients.

Probes can be removed from the membranes by immersion in boiled 0.5% SDS and cooling to room temperature. The membranes are rinsed in 2×SSC. This protocol is a modification of the method described by Church G. M. et al. (1984, "Genomic sequencing", Proc. Natl. Acad. Sci. USA, 81:1991–1995).

Figure 2:
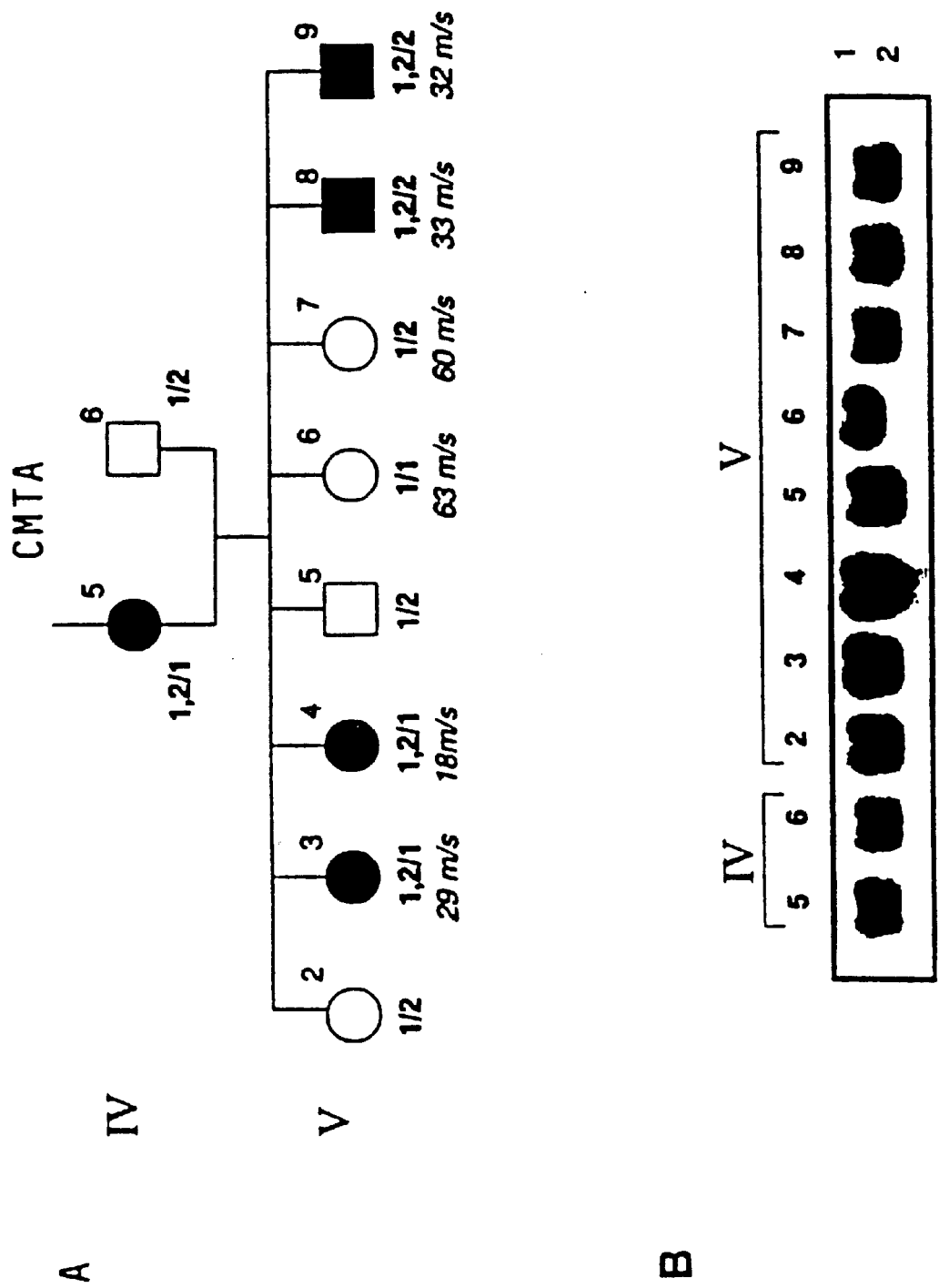
FIGS. 2A, 2B and 2C:
A. Section of the CMTA pedigree showing the haplotypes for the MspI RFLP of probe pVAW409R3. Symbols: circle, female; square, male; shaded symbol, affected individual. The Roman numeral and the number above the symbols refer to the number of the individual in the pedigree (Timmerman V. et al., 1990, Am. J. Hum. Genet. 47:680–685). The MspI haplotypes are indicated below the symbols and were constructed from the autoradiogram in FIG. 2B taking into account the duplicated allele for the CMT1a patients and the segregation of the alleles in the family. For those individuals whose NCV (Nerve Conduction Velocity) was measured, the values for the motor median nerve are written in italics below the symbol. The clinical and histopathological features of the CMT1a patients in family CMTA have been described in detail elsewhere (Raeymaekers P. et al., 1988, J. Neurol. Sci. 88:145–150). At present, family CMTA comprises 141 sampled individuals including 48 patients. In addition, NCV have been measured in 8 unaffected and 26 affected individuals, and 6 patients had a nerve biopsy.
B. Autoradiogram of the MspI Southern blot of the family members in FIG. 2A hybridized with probe pVAW409R3. Methods. Five micrograms of genomic DNA was digested overnight with 50 U of the restriction enzyme MspI at 37° C., separated by agarose gel electrophoresis, transferred to Hybond N+ (Amersham) and hybridized with radiolabeled probe pVAW409R3a. Probe pVAW409R3a is an 1.4 kb EcoRI-BamHI fragment of probe pVAW409R3, free of highly repetitive sequences. The MspI alleles 1 and 2 correspond to the restriction fragments 2.8 kb and 2.7 kb, respectively (Wright E. C. et al., 1990, Genomics 7:103–109).
C. Densitometric scanning for a heterozygous unaffected (V7) and affected (V8) individual. The autoradiogram in FIG. 2B was scanned at 600 nm in a computerized densitometer "Appraise" (Beckman Instruments Inc.). A vertical line was drawn between the two peaks and the area under the curves computed by the scanner. Density ratios of 0.81 and 1.94 were obtained for allele 2 vs. allele 1 in individuals V7 and V8, respectively.
Figure 3:
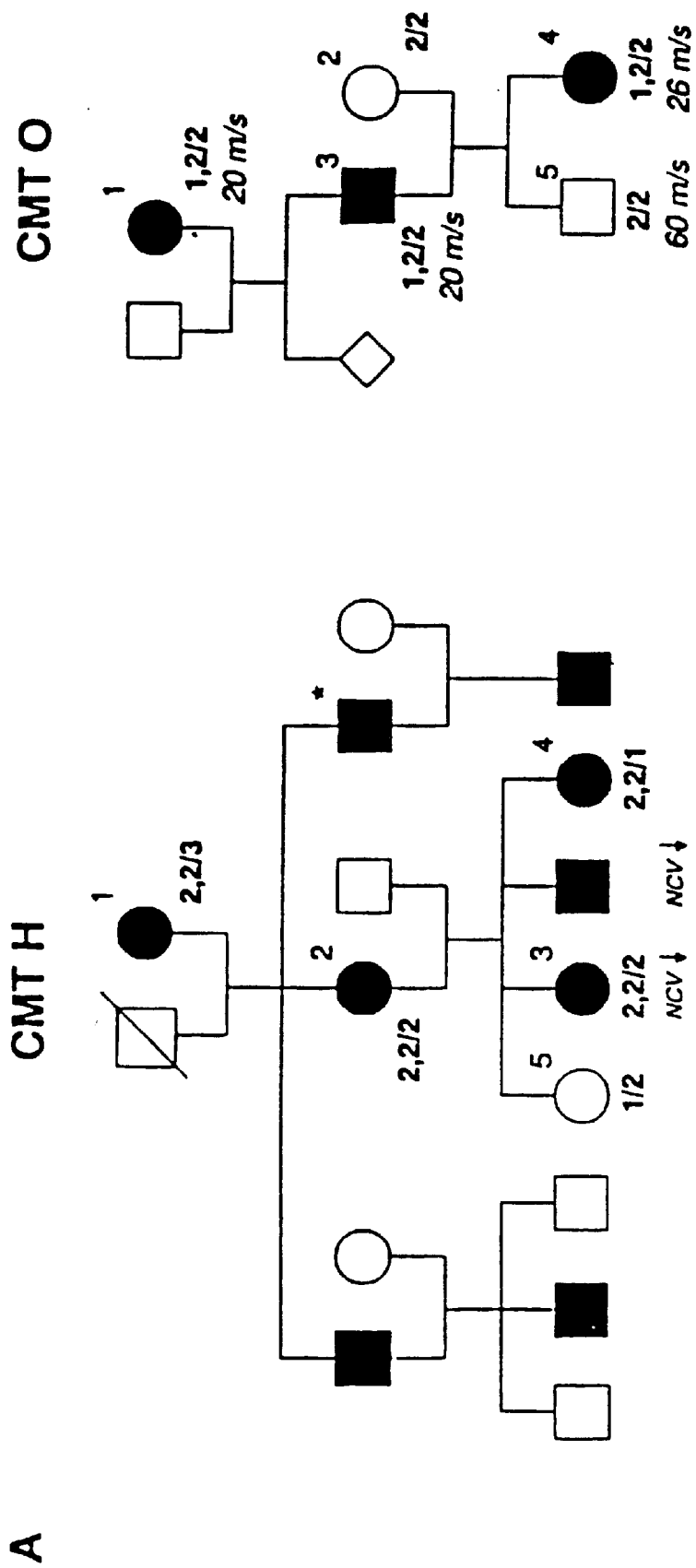
FIGS. 3A and 3B:
A. Pedigrees of families CMTH, CMTO and CMT33 showing the haplotypes for the MspI RFLP of probe pVAW409R3. Symbols as in FIG. 2A with diagonal line, deceased; diamond, section of the pedigree of which the exact genealogy is not known. The family members available for DNA analysis are indicated by a number above the symbols. As in FIG. 2A, the MspI haplotype and the motor median nerve NCV are written below the symbol. In family CMTH the affected individuals showed a 60% reduction in NCV, the patient with a nerve biopsy in families CMTH and CMT33 are indicated with an asterisk.
B. Autoradiogram of the MspI Southern blot illustrating the pVAW409R3 duplication for a pair of siblings belonging to each of the CMT1 families in FIG. 3A. The MspI alleles and methods were as in FIG. 2B.
Figure 4:
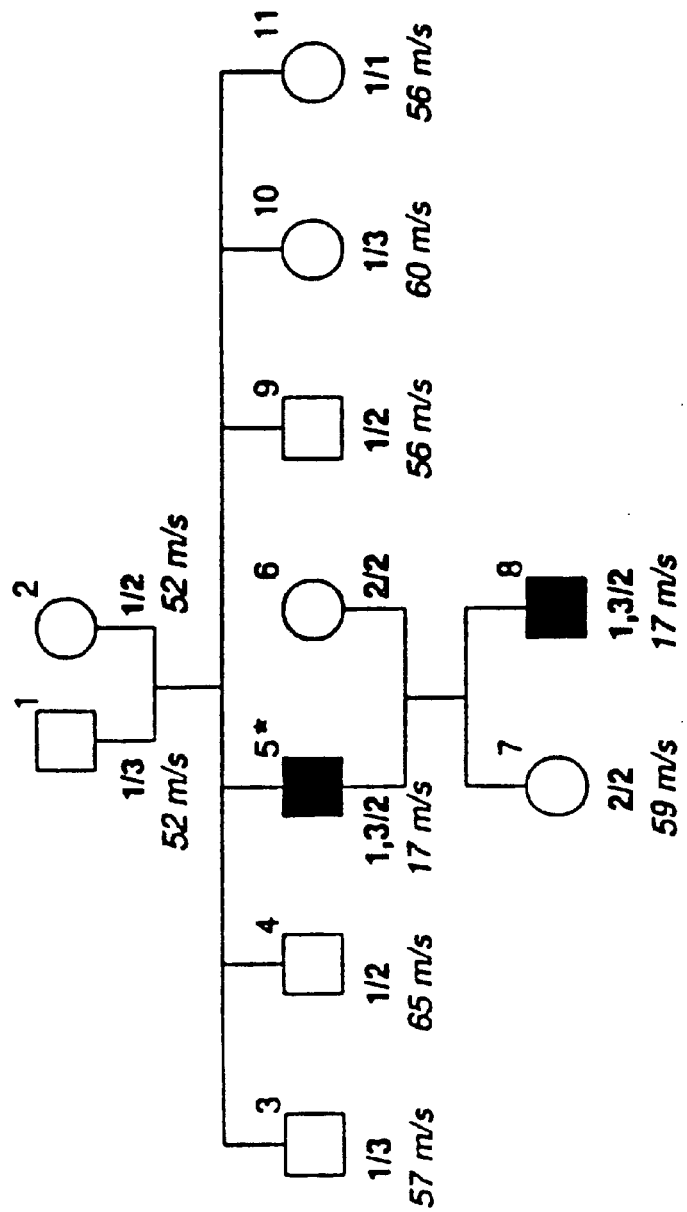
FIGS. 4A and 4B:
A. Pedigree of family CMTG. Symbols, pedigree numbers, MspI haplotypes, motor median nerve NCV and nerve biopsy as in FIG. 3A.
B. Autoradiogram of the MspI Southern blot of the family members in FIG. 4A hybridized with probe pVAW409R3 as described in FIG. 2B. The numbers 1, 2 and 3 correspond to the MspI alleles 2.8 kb, 2.7 kb and 1.9 kb, respectively (Wright E. C. et al., 1990, Genomics 7:103–109).
Figure 5:
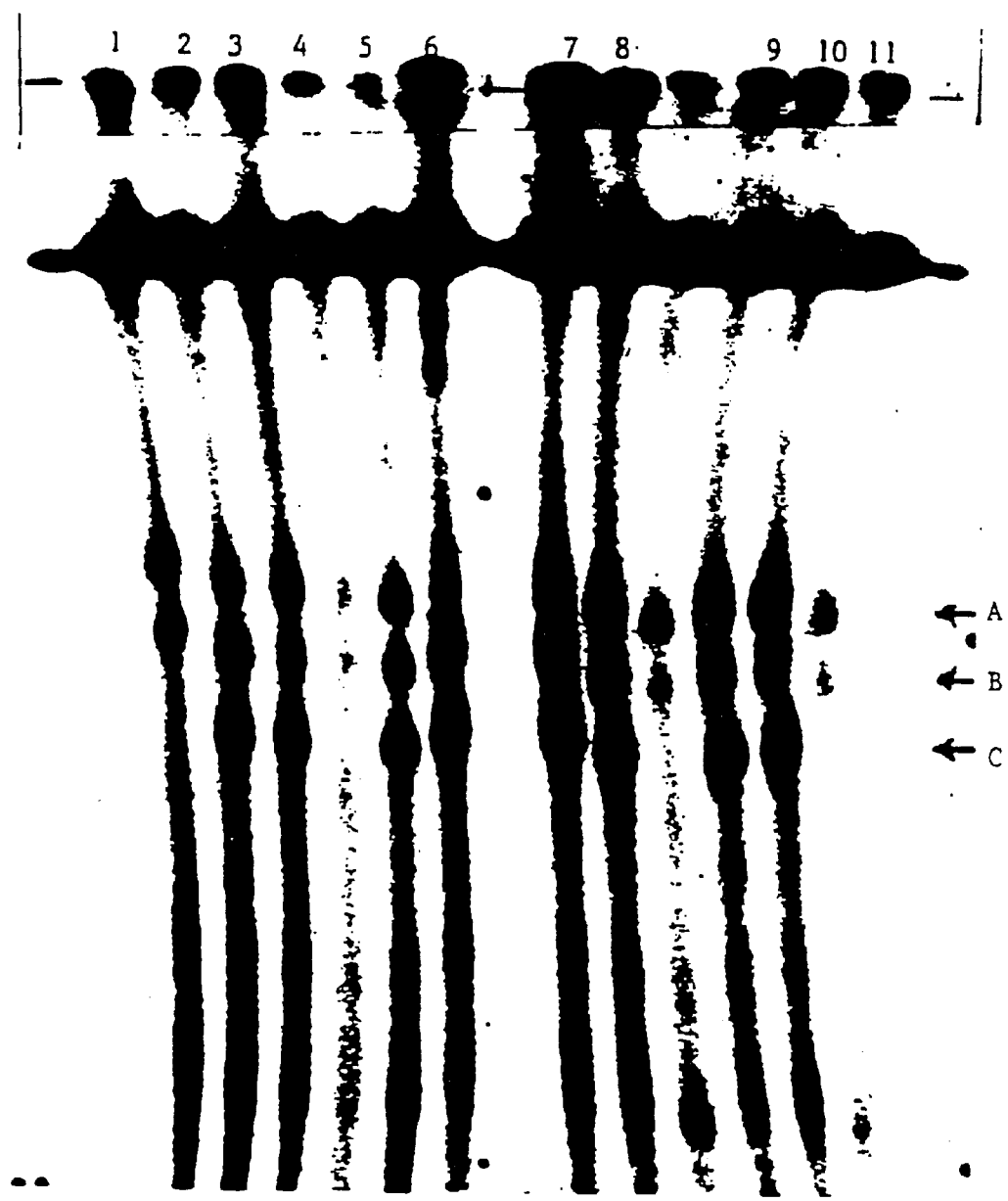
FIG. 5 represents a pulsed field gel electrophoresis of SacII digested DNA from CMT1 patients and non-patients. DNA was digested, electrophoresed and blotted onto Hybond N+ (Amersham) as described in the text. The filter was hybridized with pVAW409R3a. The same hybridization signals were obtained with any derivative of probe of pVAW409R3 and pVAW409R1.

The Difference Between Charcot-Marie-Tooth Patients and Non-affected Individuals:

This is with reference to FIGS. 2, 3 and 4. Southern blots with pVAW409R3a

The detected alleles with pVAW409R3a are 2.8, 2.7 or 1.9 kb. A normal, non-affected person always has two alleles of the MspI polymorphism of pVAW409R3a and might be heterozygous (2.8/2.7, 2.8/1.9, 2.7/1.9) or homozygous (2.8/2.8, 2.7/2.7 or 1.9/1.9). It has now been observed that a CMT1a patient carries three alleles of this polymorphism, indicating that CMT1a patients carry a duplication of the relevant area of chromosome 17. As shown in the present Figures, this can be manifested differently on Southern blots:

in family CMTG (FIG. 4), for example, the patient carries all three different alleles of the polymorphism.

in family CMTA (FIG. 2), CMTO, CMTH and CMT33 (FIG. 3), the patients have two different alleles (in these cases 2.8 and 2.7 kb, but any other combination including the 1.9 kb fragment is possible), but one of the alleles has a double intensity. This difference in intensity can often easily be observed by the eye, confirmation with a densitometer, however, can be helpful (see FIG. 2).

it is, however, also possible that the patient is homozygous, meaning that the three alleles carried are of the same size. In that case, the presence of the duplication has to be screened with a densitometer using a control hybridization with a probe from another chromosomal region (routinely SF85 from chromosome 21 can be used). In some cases, however, the presence of the mutation can also be assumed on the basis of the family history (the duplication has been observed in another patient from that family, for example, the affected parent) and the marker segregation.

Southern Blots with pVAW409R1b:

With probe pVAW409R1b, the presence of the duplication can be observed firstly by interpretation of the 3-allelic MspI polymorphism which also can be observed with pVAW409R3 and which was described earlier. This polymorphism, however, is much more vagely detected with pVAW409R1b as compared with pVAW409R3a. The presence of the duplication can also be detected on the basis of the two-allelic polymorphism detected by probe pVAW409R1b itself. The interpretation of this polymorphism with relation to the presence of the duplication is much more difficult for several reasons:

there are only two alleles, 5.3 and 2.7 kb, ruling out the chance that any patient shows three different alleles.

the different fragment sizes of the alleles (5.3 kb and 2.7 kb) make close comparison of the density of both alleles impossible. Furthermore, the interpretation of the polymorphism (especially the intensity of the hybridization fragments) is more prone to experimental variables such as DNA quality, differential efficiency of blotting in different parts of the gel, differential hybridization efficiency on different parts of the filter, etc. The use of a densitometer is nearly always necessary to evaluate the presence of the duplication.

Detection of Junction Fragments:

If a genetic disease is caused by a duplication or deletion, it is advisable to detect and clone junction fragments because these fragments not only mark the beginning and the end of the structural alteration, but also prove the existence of the structural alteration in question by the detection of an altered fragment in the DNA of the patient; by contrast, non-patients exhibit normal fragments. One is then no longer dependent on density screenings which are often prone to different (and false) interpretations.

In a first attempt, using classical agarose gel electrophoresis, it was attempted to detect these junction fragments by screening different restriction digests on Southern blots of patients and non-patients with the probes pVAW409R3 and pVAW409R1. No junction fragments were detected, indicating that the duplication might be several ten-thousands of base pairs long.

In a second attempt, rare cutter enzymes like NotI, BssHII, SacII, NaeI, NarI, SfiI, NruI, MluI, AscI, FspI, PvuI and others were used in combination with pulsed field gel electrophoresis. The DNA from patients and non-patients was digested, pulsed field electrophoresed, and hybridized with pVAW409R1a, pVAW409R3a or VAW409; supplementary bands were observed with the enzymes SacII, NarI, FspI and AscI for the DNA of patients as compared with non-patients.

With SacII and probe VAW409 and its derivatives, fragments of 500 and 550 kb were detected in normal persons, and a supplementary fragment of 450 kb was detected in CMT1a patients. Upon reanalysis with SacII and probes VAW409 and its derivatives, fragments of 600 and 550 kb were detected in normal persons, and a supplementary fragment of 500 was detected in CMT1a patients.

With AscI and probes VAW409 and its derivatives, fragments of 800 and 300 kb were detected in normal persons, and a supplementary fragment of 500 kb was detected in CMT1a patients.

With FspI and probes VAW409 and its derivatives, fragments of 800 and 600 kb were detected in normal persons, and a supplementary fragment of 500 kb was detected in CMT1a patients.

With SfiI, fragments of 300 and 800 kb were detected in normal persons, and a supplementary fragment of 600 kb was detected in CMT1a patients with VAW412 and EW401 and their derivatives.

In order to localize the CMT1a gene more precisely, a family designated CMTA was analyzed, with polymorphic markers located in 17p11.2–p12. With probe pVAW409R3 (D17S122) density differences were observed in the hybridization signals for all CMT1a patients, suggesting the presence of a duplication of the sequence in probe pVAW409R3.

Probe pVAW409R3 is localized in band 17p11.2 and recognizes a three allelic restriction fragment length polymorphism (RFLP) on MspI Southern blots with allele lengths of 2.8 kb, 2.7 kb, and 1.9 kb and frequencies of 0.51, 0.43, and 0.06, respectively, (Wright E. C. et al., 1990, Genomics 7:103–109). In FIG. 2A a representative part of the CMTA family is shown, illustrating the segregation of the pVAW409R3 duplication with CMT1a disease. As can be seen from the MspI Southern blot in FIG. 2B, two of the CMT1a children have a double density of allele 1, the other two children of allele 2, suggesting that the pVAW409R3 duplication segregates with both alleles 1 and 2 of the affected mother. Heterozygosity of the pVAW409R3 duplication is consistent throughout the whole CMTA pedigree. The presence of the duplication in the CMT1a patients was confirmed by densitometric scanning showing a two-to-one ratio of the MspI alleles (FIG. 2C).

Further, the duplication was also detected by probe pVAW409R1, a non-overlapping subclone belonging to the same D17S122 locus. Neither pVAW409R3 nor pVAW409R1 detected duplication junction fragments if the CMT1a patients' DNA was digested with different restriction enzymes, suggesting that the duplication comprises several thousands of base pairs.

The results with probe pVAW409R3 indicated that a duplication in 17p11.2 is the primary genetic defect in family CMTA. To test whether duplications are a general feature in CMT1a patients three distinct CMT1 families were analyzed with probe pVAW409R3. The MspI alleles are indicated on the pedigrees in FIG. 3A. The families CMTO, CMTH and CMT33 originate from different medical care centers in Belgium.

In each family, patients were recorded in at least three successive generations. The clinical features of the patients were consistent with CMT1, and NCV were measured in at least two affected individuals. In addition, in families CMTH and CMT33, a nerve biopsy was performed. Neither of the families had previously been tested for linkage with chromosome 17p markers. In all three CMT1 families a duplication of probe pVAW409R3 could be observed in each affected individual. In FIG. 3B, the presence and absence of the duplication is illustrated for a pair of siblings—one affected and the other unaffected—belonging to each of the CMT1 families analyzed. Segregation analysis of the MspI alleles in each family indicated that the pVAW409R3 duplication was heterozygous for the MspI RFLP in families CMTO and CMT33 and homozygous in family CMTH (FIG. 3A).

Next, family CMTG, in which CMT1 disease newly appeared in one male individual who transmitted the disease to his son, was examined. The pedigree of family CMTG is shown in FIG. 4A. The son was clinically affected. The asymptomatic father received the diagnosis of CMT1 disease based on an electrophysiological. examination indicating a major reduction in NCV and a nerve biopsy showing segmental demyelination and remyelination with numerous typical onion bulbs. Both the father's parents, his sisters, and his brothers showed no clinical signs of CMT1 disease and had normal NCV. Paternity in family CMTG was confirmed by Southern blotting with minisatellite probes (Wong Z. et al., 1987, Ann. Hum. Genet. 51:269–288).

The same protocols as the ones described for the use of VAW409 and its derivatives have been used for the probes VAW412 and its derivatives and for EW401 and its derivatives, giving rise to the same results which have been already described hereabove.

Conclusion:

The results obtained with the probes of the invention in the Belgian CMT1 pedigrees favor the hypothesis that a duplication in 17p11.2 is the primary mutation in most if not all CMT1 families.

The in vitro diagnostic process of the invention will be useful in all patients manifesting symptoms of CMT1 disease, because the majority of said patients are affected by CMT1a disease.

For the other groups of patients manifesting the symptoms of CMT1, but which are not patients affected by CMT1a disease, the in vitro process of the invention will thus enable an exclusion diagnosis.

What is claimed is:

1. A first probe comprising a nucleotide sequence of from about 15 successive nucleotides to about the total number of successive nucleotides of:
 a Not1 fragment, wherein said Not1 fragment has $1.2 \times 10^6$ base pairs and is obtainable by the process comprising the steps of:
 (a) digesting human DNA using Not1;
 (b) separating the fragments resulting from digestion;
 (c) hybridizing the resulting separated fragments with a second probe selected from the group of VAW409, pVAW409R3, pVAW409R3a, pVAW409R3b, pVAW409R1, pVAW409R1a, pVAW409R1b, pVAW409R1c, EW401, pEW401a, pEW401b, pEW401c, pEW401d, VAW412, pVAW412R3, pVAW412R3a, pVAW412R3b and pVAW412R3c, under appropriate hybridization conditions, wherein said appropriate hybridization conditions are defined by a hybridization and wash temperature of 65° C., a hybridization medium of 0.05 M $Na_2HPO_4$/$NaH_2PO_4$, pH 7.4, 1 mM EDTA and 7% SDS, and a wash medium of 0.1×SSC+0.1% SDS up to 2×SCC+0.1% SDS; and
 (d) isolating a DNA fragment that hybridizes with said second probe of step (c),
 wherein said first probe is used for the in vitro diagnosis for detecting the presence of a duplication on chromosome 17p in patients suffering from Charcot-Marie Tooth disease, and wherein said first probe is other than pVAW409R3, pEW401 or pVAW412R3.

2. A first probe comprising a nucleotide sequence of from about 15 successive nucleotides to about the total number of successive nucleotides of:
 a junction fragment of 500 kb, wherein said junction fragment of 500 kb is obtainable by a process comprising the steps of:
 (a) digesting human DNA using SacII;
 (b) separating the fragments resulting from digestion;
 (c) hybridizing the resulting separated fragments with a second probe selected from the group of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M $Na_2HPO_4$/$NaH_2PO_4$, pH 7.4, 1 mM EDTA and 7% SDS, and a wash medium of 0.1×SSC+0.1% SDS up to 2×SCC+0.1% SDS; and
 (d) isolating a 500 kb DNA fragment that hybridizes with said second probe of step (c),
 wherein said first probe is used for the in vitro diagnosis for detecting the presence of a duplication on chromosome 17p in patients suffering from Charcot-Marie Tooth disease, and wherein said first probe is other than pVAW409R3, pEW401 or pVAW412R3.

3. A first probe comprising a nucleotide sequence of from about 15 successive nucleotides to about the total number of successive nucleotides of:
 a junction fragment of 600 kb, wherein said junction fragment of 600 kb is obtainable by a process comprising the steps of:
 (a) digesting human DNA using SfiI;
 (b) separating the fragments resulting from digestion;
 (c) hybridizing the resulting separated fragments with a second probe selected from the group of EW401, pEW401a, pEW401b, pEW401c, pEW401d, VAW412, pVAW412R3, pVAW412R3a, pVAW4123b and pVAW412R3c, under appropriate hybridization conditions, wherein said appropriate hybridization conditions are defined by a hybridization and wash temperature of 65° C., a hybridization medium of 0.05 M $Na_2HPO_4$/$NaH_2PO_4$, pH 7.4, 1 mM EDTA and 7% SDS, and a wash medium of 0.1×SSC+0.1% SDS up to 2×SCC+0.1% SDS; and
 (d) isolating a 600 kb DNA fragment that hybridizes with said second probe of step (c),
 wherein said probe is used for the in vitro diagnosis for detecting the presence of a duplication on chromosome 17p in patients suffering from Charcot-Marie Tooth disease, and wherein said first probe is other than pVAW409R3, pEW401 or pVAW412R3.

4. The first probe according to claim 1, wherein said first probe comprises a sequence of from about 15 successive nucleotides to about the total number of successive nucleotides of the sequence of pVAW409R3a, pVAW409R3b, pVAW409R1a, pVAW409R1b, or pVAW409R1c.

5. The first probe according to claim 1, wherein said first probe comprises a sequence of from about 15 successive nucleotides to about the total number of successive nucleotides of the sequence of pEW401a, pEW401b, pEW401c, or pEW401d.

6. The first probe according to claim 1, wherein said first probe comprises a sequence of from about 15 successive nucleotides to about the total number of successive nucleotides of the sequence pVAW412R3a, pVAW412R3b or pVAW412R3c.

7. The first probe according to claim 1, wherein said first probe comprises a sequence of from about 15 successive nucleotides to about the total number of successive nucleotides of any sequence of said NotI fragment wherein said sequence is located in between any of the following sequences: pVAW409R1, pVAW409R3, EW401 and VAW412.

8. The first probe according to claim 1, wherein said first probe is pVAW409R3a, pVAW409R3b, pVAW409R1a, pVAW409R1b, pVAW409R1c, pEW401a, pEW401b, pEW401c, pEW401d, pVAW412R3a, pVAW412R3b or pVAW412R3c.

9. A method for the in vitro diagnosis of Charcot-Marie Tooth disease in patients carrying a duplication of chromosome 17p, said method comprising the step of detecting a duplication of a part of chromosome 17p in either one of the three loci D17S122, D17S125, D17S61, or in two loci or in all three loci.

10. A method for the in vitro diagnosis of Charcot-Marie Tooth disease in patients based on the detection of a duplication of a part of chromosome 17p in either one of the three loci D17S122, D17S125, D17S61, or in two loci or in three loci, said method comprising the steps of
 (a) hybridizing DNA isolated from a biological sample taken from a patient with a first probe comprising a nucleotide sequence of from about 15 successive nucleotides to about the total number of successive nucleotides of:
 a Not1 fragment, wherein said Not1 fragment has $1.2 \times 10^6$ base pairs and is obtainable by:
 digesting human DNA using Not1;
 separating the fragments resulting from digestion;
 hybridizing the resulting separated fragments with a second probe selected from the group of VAW409, pVAW409R3, pVAW409R3a, pVAW409R3b, pVAW409R1, pVAW409R1a, pVAW409R1b, pVAW409R1c, EW401, pEW401a, pEW401b, pEW401c, pEW401d, VAW412, pVAW412R3, pVAW412R3a, pVAW412R3b and pVAW412R3c, under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and isolating a DNA fragment that hybridizes with said second probe, under the appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and (b) detecting the hybridization complexes formed, thereby to detect said duplication.

11. The method according to claim 10, wherein the said first probe is selected from the group of pVAW409R1, pVAW409R3, pVAW412R3 and EW401.

12. The method according to claim 10, wherein the said first probe is selected from the group of pVAW409R3a, pVAW409R3b, pVAW409R1a, pVAW409R1b, pVAW409R1c, pVAW412R3a, pVAW412R3b, pVAW412R3c, pEW401a, pEW401b, pEW401c and pEW401d.

13. A method for the in vitro diagnosis of Charcot-Marie Tooth disease patients based on the detection of a duplication of a part of chromosome 17p in either one of the three loci D17S122, D17S125, D17S61, or in two loci or in all three loci, said method comprising the steps of:

(a) isolating DNA from a biological sample taken from a patient;

(b) digesting said isolated DNA with a restriction enzyme;

(c) separating the digested DNA by gel electrophoresis;

(d) hybridizing said digested separated DNA with a first probe comprising a nucleotide sequence of from about 15 successive nucleotides to about the total number of successive nucleotides of:

a Not1 fragment, wherein said Not1 fragment has 1.2×10$^6$ base pairs and is obtainable by:
digesting human DNA using Not1;
separating the fragments resulting from digestion;
hybridizing the resulting separated fragments with a second probe selected from the group of VAW409, pVAW409R3, pVAW409R3a, pVAW409R3b, pVAW409R1, pVAW409R1a, pVAW409R1b, pVAW409R1c, EW401, pEW401a, pEW401b, pEW401c, pEW401d, VAW412, pVAW412R3, pVAW412R3a, pVAW412R3b and pVAW412R3c, under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and isolating a DNA fragment that hybridizes with said second probe, under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+ 0.1% SDS up to 2×SCC+0.1% SDS; and (e) detecting the duplication by:
(e1) detecting more than two allelic DNA fragments, or
(e2) screening the intensity of DNA fragments, or
(e3) screening for supplementary fragments with respect to fragments of patients who do not have Charcot-Marie Tooth disease, or
(e4) screening for a junction fragment.

14. The method according to claim 13, wherein said restriction enzyme of step (b) is a polymorphic restriction enzyme which gives rise to three allelic fragments, and wherein the more than two allelic DNA fragments of step (e1) consist of three allelic DNA fragments.

15. The method according to claim 13, wherein said restriction enzyme of step (b) is a polymorphic restriction enzyme giving rise to two allelic fragments and wherein step (e2) includes the screening of the intensity of two allelic fragments, one of them having an intensity corresponding to about twice the intensity with respect to the other allelic fragment.

16. The method according to claim 13, wherein step (e) includes the screening of constant fragments, said constant fragments showing an intensity of about 1.5 times intensity obtained for the same fragments in a patent who does not have Charcot-Marie Tooth disease.

17. The method according to claim 13, wherein the restriction enzyme used in step (b) is MspI, and wherein the first probe of step (d) is pVAW409R3, pVAW409R3a or pVAW409R3b and wherein the detection of the dupolication of step (e) comprises at least one of the following process:

detecting three allelic fragments of 2.9 kb, 2.8 kb and 1.9 kb, or detecting a combination of two allelic fragments selected from the group of 2.9 kb, 2.8 kb and 1.9 kb, with one of the allelic fragments having an intensity corresponding to about twice the intensity with respect to the other allelic fragment, or detecting one allelic fragment chosen from among 2.9 kb, 2.8 kb and 1.9 kb, wherein said one alelic fragment has:
an intensity corresponding to about three times the intensity obtained for the same fragments in a heterozygous patient who does not have Charcot-Marie Tooth disease, or
an intensity corresponding to about 1.5 times the intensity obtained for the same fragment in a homozygous patient who does not have Charcot-Marie Tooth disease.

18. The method according to claim 17, wherein said first probe is pVAW409R3a.

19. The method according to claim 13, wherein the restriction enzyme of step (b) is MspI, and wherein the first probe of step (d) is pVAW409R1or pVAW409R1b, and wherein the detection of the duplication of step (e) comprises at least one of the following processes:

detecting three allelic fragments of 2.9 kb, 2.8 kb and 1.9 kb, or detecting a combination of two allelic fragments selected from the group of 2.9 kb, 2.8 kb and 1.9 kb, with one of the allelic fragments having an intensity corresponding to about twice the intensity with respect to the other allelic fragment, or detecting one allelic fragment having:
an intensity corresponding to about three times the intensity obtained for the same fragments in a heterozygous patient who does not have Charcot-Marie Tooth disease, or an intensity corresponding to about 1.5 times the intensity obtained for the same fragments in a heterozygous patient who does not have Charcot-Marie Tooth disease, or detecting a MspI polymorphism of two different allelic fragments of 5.3 kb and 2.7 kb, one of them having a intensity corresponding to twice the intensity with respect to other one, or detecting one allelic fragment of these two allelic fragments, wherein said allelic fragment which is detected has:

an intensity corresponding to about three times the intensity obtained for the same fragments in a heterozygous patient who does not have Charcot-Marie Tooth disease, or an intensity corresponding to about 1.5 times the intensity obtained for the same fragments in a heterozygous patient who does not have Charcot-Marie Tooth disease.

20. The method according to claim 19, wherein said first probe is pVAW409R1b.

21. The method according to claim 13, wherein the restriction enzyme of step (b) is MspI and wherein the first probe of step (d) is pVAW409R1a and wherein the detection of the dupoication of step (e) comprises teh detection of constant MspI fragments having an intensity corresponding to about 1.5 time the intensity obtained for the same fragments in a patient who does not have Charcot-Marie Tooth disease.

22. The method according to claim 13, wherein the restriction enzyme of step (b) is MspI, and wherein the first probe of step (d) is pVAW409R1c and wherein the detection of the duplication of step (e) comprises at least one of the following processes:

detecting a MspI polymorphism of two different allelic fragments of 5.3 kb and 2.7 kb, one of them having an intensity corresponding to twice the intensity with respect to the other one, or detecting one allelic fragment of these two allelic fragments, wherein said allelic fragment which is detected has:

an intensity corresponding to about three times the intensity obtained for the same fragments in a heterozygous patient who does not have Charcot-Marie Tooth disease, or an intensity corresponding to about 1.5 times the intensity obtained for the same fragments in a heterozygous patient who does not have Charcot-Marie Tooth disease.

23. The method according to claim 13, wherein the restriction enzyme of step (b) is MspI, and wherein the first probe of step (d) is EW401, pEW401a, pEW401b, pEW401c or pEW401d, and wherein the detection of the duplication of step (e) comprises at least one of the following processes:

detecting two allelic MspI fragments respectively of 5.5 kb and 4.4 kb, with one of the allelic fragments having an intensity corresponding to twice that of the other allelic fragment, or detecting one allelic fragment chosen from among 5.5 kb and 4.4 kb, wherein said allelic fragment which is detected has:

an intensity corresponding to about three times the intensity obtained for the same fragment in a heterozygous patient who does not have Charcot-Marie Tooth disease, or an intensity corresponding to about 1.5 times the intensity obtained for the same fragments in a heterozygous patient who does not have Charcot-Marie Tooth disease.

24. The method according to claim 13, wherein the restriction enzyme of step (b) is MspI, and wherein the first probe of step (d) is pVAW412R3 and wherein the detection of the duplication of step (e) comprises the simultaneous detection of two diallelic MspI polymorphisms corresponding respectively to fragments of 10.5 kb and 5.4 kb and to fragments of 2.6 kb and 1.9+0.7 kb.

25. The method according to claim 13, wherein the restriction enzyme of step (b) is SacII, and wherein the separating step of step (c) is done by pulsed field gel electrophoresis, wherein the first probe of step (d) is selected from the group of VAW409, pVAW409R1a, pVAW409R1b, pVAW409R1c, pVAW409R3a and pVAW409R3b, and wherein the detection of the duplication of step (e4) comprises the detection of a SacII junction fragment of 500 kb.

26. The method according to claim 13, wherein the restriction enzyme of step (b) is SfiI, and wherein the separating step of step (c) is done by pulsed field gel electrophoresis, and wherein the first probe of step (d) is selected from the group of VAW412, pVAW412R3, pVAW412R3b, pVAW412R3c, EW401, pEW401a, pEW401b, pEW401c and EW401d, and wherein the detection of the duplication of step (e4) comprises the detection of a SfiI junction fragment of 600 kb.

27. A method for the in vitro diagnosis of Charcot-Marie Tooth disease in a patient carrying a duplication of a part of chromosome 17p which comprises the step of detecting a duplication of the patients' PMP-22 gene, located within said duplication.

28. The method according to claim 27, wherein the PMP-22 gene is the PMP-22/GAS-3 gene.

29. A method for the diagnosis of Charcot-Marie Tooth disease in a patient carrying a duplication of a part of chromosome 17p, said method comprising the steps of:

(a) hybridizing the DNA taken from a biological sample of said patient with a first probe comprising a nucleotide sequence of from about 15 successive nucleotides to about the total number of successive nucleotides of:

a Not1 fragment, wherein said Not1 fragment has $1.2 \times 10^6$ base pairs and is obtainable by:

digesting human DNA using Not1;

separating the fragments resulting from digestion;

hybridizing the resulting separated fragments with a second probe selected from the group of VAW409, pVAW409R3, pVAW409R3a, pVAW409R3b, pVAW409R1, pVAW409R1a, pVAW409R1b, PVAW409R1c, EW401, pEW401a, pEW401b, pEW401c, pEW401d, VAW412, pVAW412R3, pVAW412R3a, pVAW412R3b and pVAW412R3c, under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and isolating a DNA fragment that hybridizes with said second probe, under the appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+ 0.1% SDS up to 2×SCC+0.1% SDS;
(b) detecting the hybridization complex which has been formed; and
(c) detecting whether the intensity obtained with the hybridization complex corresponds to 1.5 times the intensity obtained in patients who do not have Charcot-Marie Tooth disease.

30. The method according to claim 29, further comprising amplifying by means of a DNA primer set a DNA fragment present in the biological sample, said fragment containing the duplication of part of chromosome 17p.

31. A method for the in vitro diagnosis of Charcot-Marie Tooth disease in a patient carrying a duplication of part of chromosome 17p, said method comprising the steps of:
(a) amplifying a fragment of a duplicated part of chromosome 17p, which fragment is contained in a biological sample taken from said patient, with the following DNA primer set:
right primer:
5' CAT ACA ATG CAC GCA GTT GA 3' (SEQ ID NO:2) bp-position 601,
left primer:
5' AAA CCC AGA ACT TCC ACT TC 3' (SEQ ID NO:3) bp-position 875, or
right primer:
5' CAT ACA ATG CAC GCA GTT GA 3' (SEQ ID NO:2) bp-position 601,
left primer:
5' TTG GTA CAA CCT TCC TGG AG 3' (SEQ ID NO:4) bp-position 940;
(b) amplifying a sequence outside the duplication of a part of chromosome 17p, contained in a biological sample taken from said patient, with the following DNA primer set:
right primer:
5' CAA ATC CTG CCC ATG AAG TT 3' (SEQ ID NO:5) bp-position 9,
left primer:
5' ATG TAT TGG GCT GGT TAC TG 3' (SEQ ID NO:6) bp-position 199, or
right primer:
5' ATC CAT TCA TCC ATT CTC CC 3' (SEQ ID NO:7),
left primer:
5' CAA CAT CAG GTC AAC CAG AG 3' (SEQ ID NO:8); and
(c) comparing the amount of the amplified fragment located within the duplication of a part of chromosome 17p and the amount of the amplified sequence outside the duplication, which is in the ratio of 3/2 if said patient suffers from Charcot-Marie Tooth disease.

32. A kit for the in vitro diagnosis of Charcot-Marie Tooth disease in patients carrying a duplication on chromosome 17p, said kit comprising a determined amount of a first nucleotide probe according to claim 1.

33. The kit according to claim 32, further comprising a probe for a PMP-22 gene.

34. A kit for the in vitro diagnosis of Charcot-Marie Tooth disease in a patient carrying a duplication of part of chromosome 17p said kit comprising:
(a) a set of primers able to amplify a DNA fragment of the duplication of a part of chromosome 17p, and with said set of primers chosen from among:
right primer:
5' CAT ACA ATG CAC GCA GTT GA 3' (SEQ ID NO:2) bp-position 601,
left primer:
5' AAA CCC AGA ACT TCC ACT TC 3' (SEQ ID NO:3) bp-position 875, or
right primer:
5' CAT ACA ATG CAC GCA GTT GA 3' (SEQ ID NO:2) bp-position 601,
left primer:
5' TTG GTA CAA CCT TCC TGG AG 3' (SEQ ID NO:4) bp-position 940;
(b) a set of primers that amplify a DNA fragment of the duplication of a part of chromosome 17p and with said set of primers chose from among:
right primer:
5' CAA ATC CTG CCC ATG AAG TT 3' (SEQ ID NO:5) bp-position 9,
left primer:
5' ATG TAT TGG GCT GGT TAC TG 3' (SEQ ID NO:6) bp-position 199, or
right primer:
5' ATC CAT TCA TCC ATT CTC CC 3' (SEQ ID NO:7),
left primer:
5' CAA CAT CAG GTC AAC CAG AG 3' (SEQ ID NO:8).

35. A method for the in vitro diagnosis of Charcot-Marie Tooth disease in patients based on the detection of a duplication of a part of chromosome 17p in either one of the three loci D17S122, D17S125, D17S61, or in two loci or in three loci, said method comprising the steps of
(a) hybridizing DNA isolated from a biological sample taken from a patient with a first probe comprising a nucleotide sequence of from about 15 successive nucleotides to about the total number of successive nucleotides of:
a junction fragment of 500 kb, wherein said junction fragment is obtainable by:
digesting human DNA using SacII;
separating the fragments resulting from digestion;
hybridizing the resulting separated fragments with a second probe selected from the group consisting of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and
isolating a 500 kb DNA fragment that hybridizes with said second probe, under the appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+ 0.1% SDS; and
(b) detecting the hybridization complexes formed, thereby to detect said duplication.

36. A method for the in vitro diagnosis of Charcot-Marie Tooth disease patients based on the detection of a duplication of a part of chromosome 17p in either one of the three loci D17S122, D17S125, D17S61, or in two loci or in all three loci, said method comprising the steps of:
(a) isolating DNA from a biological sample taken from a patient;
(b) digesting said isolated DNA with a restriction enzyme;
(c) separating the digested DNA by gel electrophoresis;
(d) hybridizing said digested separated DNA with a first probe comprising a nucleotide sequence of from about 15 successive nucleotides to about the total number of successive nucleotides of:
a junction fragment of 500 kb, wherein said junction fragment is obtainable by:
digesting human DNA using SacII;
separating the fragments resulting from digestion;
hybridizing the resulting separated fragments with a second probe selected from the group consisting of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and
isolating a 500 kb DNA fragment that hybridizes with said second probe, under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and
(e) detecting the duplication by:
(e1) detecting more than two allelic DNA fragments, or
(e2) screening the intensity of DNA fragments, or
(e3) screening for supplementary fragments with respect to fragments of patients who do not have Charcot-Marie Tooth disease, or
(e4) screening for a junction fragment.

37. A method for the diagnosis of Charcot-Marie Tooth disease in a patient carrying a duplication of a part of chromosome 17p, said method comprising the steps of:
(a) hybridizing the DNA taken from a biological sample of said patient with a first probe comprising a nucleotide sequence of from about 15 successive nucleotides to about the total number of successive nucleotides of:
a junction fragment of 500 kb, wherein said junction fragment is obtainable by:
digesting human DNA using SacII;
separating the fragments resulting from digestion;
hybridizing the resulting separated fragments with a second probe selected from the group consisting of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and
isolating a 500 kb DNA fragment that hybridizes with said second probe, under the appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS;
(b) detecting the hybridization complex which has been formed; and
(c) detecting whether the intensity obtained with the hybridization complex corresponds to 1.5 times the intensity obtained in patients who do not have Charcot-Marie Tooth disease.

38. A method for the in vitro diagnosis of Charcot-Marie Tooth disease in patients based on the detection of a duplication of a part of chromosome 17p in either one of the three loci D17S122, D17S125, D17S61, or in two loci or in three loci, said method comprising the steps of
(a) hybridizing DNA isolated from a biological sample taken from a patient with a first probe comprising a nucleotide sequence of from about 15 successive nucleotides to about the total number of successive nucleotides of:
a junction fragment of 600 kb, wherein said junction fragment of 600 kb is obtainable by:
digesting human DNA using SfiI;
separating the fragments resulting from digestion;
hybridizing the resulting separated fragments with a second probe selected from the group consisting of EW401, pEW401a, pEW401b, pEW401c, pEW401d, VAW412, pVAW412R3, pVAW412R3a, pVAW412R3b and pVAW412R3c, under appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and
isolating a DNA fragment that hybridizes with said second probe, under the appropriate hybridization conditions, wherein said appropriate hybridization conditions are defined by a hybridization and wash temperature of 65° C., a hybridization medium of 0.05 M Na$_2$HPO$_4$/NaH$_2$PO$_4$, pH 7.4, 1 mM EDTA and 7% SDS, and a wash medium of 0.1×SSC+0.1% SDS up to 2×SCC+0.1% SDS; and
(b) detecting the hybridization complexes formed, thereby to detect said duplication.

39. A method for the in vitro diagnosis of Charcot-Marie Tooth disease patients based on the detection of a duplication of a part of chromosome 17p in either one of the three loci D17S122, D17S125, D17S61, or in two loci or in all three loci, said method comprising the steps of:
(a) isolating DNA from a biological sample taken from a patient;
(b) digesting said isolated DNA with a restriction enzyme;
(c) separating the digested DNA by gel electrophoresis;
(d) hybridizing said digested separated DNA with a first probe comprising a nucleotide sequence of from about 15 successive nucleotides to about the total number of successive nucleotides of:
a junction fragment of 600 kb, wherein said junction fragment of 600 kb is obtainable by:
digesting human DNA using SfiI;
separating the fragments resulting from digestion;

hybridizing the resulting separated fragments with a second probe selected from the group consisting of EW401, pEW401a, pEW401b, pEW401c, pEW401d, VAW412, pVAW412R3, pVAW412R3a, pVAW412R3b and pVAW412R3c, under appropriate hybridization conditions, wherein said appropriate hybridization conditions are defined by a hybridization and wash temperature of 65° C., a hybridization medium of 0.05 M $Na_2HPO_4/NaH_2PO_4$, pH 7.4, 1 mM EDTA and 7% SDS, and a wash medium of 0.1×SSC+0.1% SDS up to 2×SCC+0.1% SDS; and isolating a DNA fragment that hybridizes with said second probe, under appropriate hybridization conditions, wherein said appropriate hybridization conditions are defined by a hybridization and wash temperature of 65° C., a hybridization medium of 0.05 M $Na_2HPO_4/NaH_2PO_4$, pH 7.4, 1 mM EDTA and 7% SDS, and a wash medium of 0.1×SSC+ 0.1% SDS up to 2×SCC+0.1% SDS; and (e) detecting the duplication by:
  (e1) detecting more than two allelic DNA fragments, or
  (e2) screening the intensity of DNA fragments, or
  (e3) screening for supplementary fragments with respect to fragments of patients who do not have Charcot-Marie Tooth disease, or
  (e4) screening for a junction fragment.

40. A method for the diagnosis of Charcot-Marie Tooth disease in a patient carrying a duplication of a part of chromosome 17p, said method comprising the steps of:

(a) hybridizing the DNA taken from a biological sample of said patient with a first probe comprising a nucleotide sequence of from about 15 successive nucleotides to about the total number of successive nucleotides of:

a junction fragment of 600 kb, wherein said junction fragment of 600 kb is obtainable by:
  digesting human DNA using SfiI;
  separating the fragments resulting from digestion;
  hybridizing the resulting separated fragments with a second probe selected from the group consisting of EW401, pEW401a, pEW401b, pEW401c, pEW401d, VAW412, pVAW412R3, pVAW412R3a, pVAW412R3b and pVAW412R3c, under appropriate hybridization conditions, wherein said appropriate hybridization conditions are defined by a hybridization and wash temperature of 65° C., a hybridization medium of 0.05 M $Na_2HPO_4/NaH_2PO_4$, pH 7.4, 1 mM EDTA and 7% SDS, and a wash medium of 0.1×SSC+0.1% SDS up to 2×SCC+0.1% SDS; and
  isolating a DNA fragment that hybridizes with said second probe, under the appropriate hybridization conditions, wherein said appropriate hybridization conditions are defined by a hybridization and wash temperature of 65° C., a hybridization medium of 0.05 M $Na_2HPO_4/NaH_2PO_4$, pH 7.4, 1 mM EDTA and 7% SDS, and a wash medium of 0.1×SSC+ 0.1% SDS up to 2×SCC+0.1% SDS;

(b) detecting the hybridization complex which has been formed; and (c) detecting whether the intensity obtained with the hybridization complex corresponds to 1.5 times the intensity obtained in patients who do not have Charcot-Marie Tooth disease.

41. A first probe comprising a nucleotide sequence of from about 15 successive nucleotides to about the total number of successive nucleotides of:

a junction fragment of 500 kb, wherein said junction fragment of 500 kb is obtainable by a process comprising the steps of:
  (a) digesting human DNA using FspI or AscI;
  (b) separating the fragments resulting from digestion;
  (c) hybridizing the resulting separated fragments with a second probe selected from the group of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M $Na_2HPO_4/NaH_2PO_4$, pH 7.4, 1 mM EDTA and 7% SDS, and a wash medium of 0.1×SSC+0.1% SDS up to 2×SCC+0.1% SDS; and
  (d) isolating a 500 kb DNA fragment that hybridizes with said second probe of step (c), wherein said first probe is used for the in vitro diagnosis for detecting the presence of a duplication on chromosome 17p in patients suffering from Charcot-Marie Tooth disease, and wherein said first probe is other than pVAW409R3, pEW401 or pVAW412R3.

42. A method for the in vitro diagnosis of Charcot-Marie Tooth disease in patients based on the detection of a duplication of a part of chromosome 17p in either one of the three loci D17S122, D17S125, D17S61, or in two loci or in three loci, said method comprising the steps of (a) hybridizing DNA isolated from a biological sample taken from a patient with a first probe comprising a nucleotide sequence of from about 15 successive nucleotides to about the total number of successive nucleotides of:

a junction fragment of 500 kb, wherein said junction fragment is obtainable by:
  digesting human DNA using FspI or AscI;
  separating the fragments resulting from digestion;
  hybridizing the resulting separated fragments with a second probe selected from the group consisting of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M $Na_2HPO_4/NaH_2PO_4$, pH 7.4, 1 mM EDTA and 7% SDS, and a wash medium of 0.1×SSC+0.1% SDS up to 2×SCC+0.1% SDS; and
  isolating a 500 kb DNA fragment that hybridizes with said second probe, under the appropriate hybridization conditions, wherein said appropriate hybridization conditions are defined by a hybridization and wash temperature of 65° C., a hybridization medium of 0.05 M $Na_2HPO_4/NaH_2PO_4$, pH 7.4, 1 mM EDTA and 7% SDS, and a wash medium of 0.1×SSC+0.1% SDS up to 2×SCC+ 0.1% SDS; and (b) detecting the hybridization complexes formed, thereby to detect said duplication.

43. A method for the in vitro diagnosis of Charcot-Marie Tooth disease patients based on the detection of a duplication of a part of chromosome 17p in either one of the three loci D17S122, D17S125, D17S61, or in two loci or in all three loci, said method comprising the steps of:

(a) isolating DNA from a biological sample taken from a patient;

(b) digesting said isolated DNA with a restriction enzyme;
(c) separating the digested DNA by gel electrophoresis;
(d) hybridizing said digested separated DNA with a first probe comprising a nucleotide sequence of from about 15 successive nucleotides to about the total number of successive nucleotides of:
  a junction fragment of 500 kb, wherein said junction fragment is obtainable by:
    digesting human DNA using FspI or AscI;
    separating the fragments resulting from digestion;
    hybridizing the resulting separated fragments with a second probe selected from the group consisting of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M $Na_2HPO_4$/$NaH_2PO_4$, pH 7.4, 1 mM EDTA and 7% SDS, and a wash medium of 0.1×SSC+0.1% SDS up to 2×SCC +0.1% SDS; and
    isolating a 500 kb DNA fragment that hybridizes with said second probe, under appropriate hybridization conditions, wherein said appropriate hybridization conditions are defined by a hybridization and wash temperature of 65° C., a hybridization medium of 0.05 M $Na_2HPO_4$/$NaH_2PO_4$, pH 7.4, 1 mM EDTA and 7% SDS, and a wash medium of 0.1×SSC+0.1% SDS up to 2×SCC+0.1% SDS; and
(e) detecting the duplication by:
  (e1) detecting more than two allelic DNA fragments, or
  (e2) screening the intensity of DNA fragments, or
  (e3) screening for supplementary fragments with respect to fragments of patients who do not have Charcot-Marie Tooth disease, or
  (e4) screening for a junction fragment.

44. A method for the diagnosis of Charcot-Marie Tooth disease in a patient carrying a duplication of a part of chromosome 17p, said method comprising the steps of:
(a) hybridizing the DNA taken from a biological sample of said patient with a first probe comprising a nucleotide sequence of from about 15 successive nucleotides to about the total number of successive nucleotides of:
  a junction fragment of 500 kb, wherein said junction fragment is obtainable by:
    digesting human DNA using FspI or AscI;
    separating the fragments resulting from digestion;
    hybridizing the resulting separated fragments with a second probe selected from the group consisting of VAW409, pVAW409R3, pVAW409R3a, pVAW409R3b, pVAW409R1, pVAW409R1a, pVAW409R1b and pVAW409R1c under appropriate hybridization conditions, wherein said appropriate hybridization conditions are defined by a hybridization and wash temperature of 65° C., a hybridization medium of 0.05 M $Na_2HPO_4$/$NaH_2PO_4$, pH 7.4, 1 mM EDTA and 7% SDS, and a wash medium of 0.1×SSC+0.1% SDS up to 2×SCC+0.1% SDS; and
    isolating a 500 kb DNA fragment that hybridizes with said second probe, under the appropriate hybridization conditions, wherein said appropriate hybridization conditions are defined by a hybridization and wash temperature of 65° C., a hybridization medium of 0.05 M $Na_2HPO_4$/$NaH_2PO_4$, pH 7.4, 1 mM EDTA and 7% SDS, and a wash medium of 0.1×SSC+0.1% SDS up to 2×SCC+0.1% SDS;
(b) detecting the hybridization complex which has been formed; and
(c) detecting whether the intensity obtained with the hybridization complex corresponds to 1.5 times the intensity obtained in patients who do not have Charcot-Marie Tooth disease.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2133 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CTTTTGTAAA GTAATATTTG TTACTTATAT TTTCTAACTA TGAAAATAAC CCTACCTGAT      60

GCAGAAGTCC TAGAAAAACA CAGACAAGGC CGGGTGCGGT GGCTCACACC TAATCCCTGC     120

ACTTTGGGAT GCTGAGATAG GAGGATCAGT TGAGGTCAGG AGTTCGAGAC CAGCCTGACG     180

AACATGGTGA ANCCCGTCTC TACTAAAAAT ACAAAAATTA GCCAGGCATG GTGGTGGGTG     240

CTTGTAATCC CAGCTACTCA GGAGGCTGAG GCAGGAGAAT CACTTCGAAC CTGGAAGGAG     300

AGGTTGCAGT GAGCCGAGAT TTGGCCACTG CACTCCAGCC TGGGTGACAG AGTGAGACTC     360

TGTCTCAAAA AAAGAAAAAA AAAAGAAAAA CACAGACAAG CCACAAGTTG CCATGTATAG     420

CATGCCCTGG ATGCTGTGGG ATACAGGCTG AAAACAGCTT GATGCCTTTC CTACCACAGC     480

TTGTTCAACT TACCCCACCA GTGGTTTCTT TGCCAGGCCC CTGGATGCAA TTTTGGGCAG     540

GATCCATGGT CTCTTCCAGC CACTTTCTTA AAAAGTTAA  CTTGATTGAA ATTCACATAC     600

CATACAATGC ACGCAGTTGA AATATAGCCT GTCTGATTTT TCAGTAACAT TGTCTGTAAA     660

ATAAATATCT ACTTTAACAT GAATTTGCCT GGTATATGGA TTACTTTTTT GAATGTACCA     720

TAATCAACCT TTTTGTTTTA AACTTTTGAG CATTTAGGTA GTTTCTCATT TTTCAGGGAT     780

CAGCATAAAT ATGGCTGAAA TGAATATCCT CACACGTATA TCCTTGGGTA CATTGTTTCT     840
```

```
TATAATACAT TTCTAGAAGT GGAAGTTCTG GGTTTTCCAC ATTTGAATGA AAGGCTGTTG        900

GTTTGTGTTG CCTCTTTACC CTCCAGGAAG GTTGTACCAA TTCAACATTC TCATCTGTAT        960

TATACAGAGA AACTTTTTCT AAATATGCTC GCCAGCACTG CAAATGATCA TTCTCTCTAC       1020

TCCTGCTAAT ATTTCCTTAG TAGGCTGTTT TCATTAATGC TTCTTTGATT AGCCCTTGAG       1080

GCTGAGTATT TTGTCATATG GCTTATTGAT GTGATGTGTG ACACATTTAT AATGAACCTA       1140

CACGTTCACA TCATTCATTA ATCCTTTTGG CCCCTTGAAA CTGGCAGAAG AAGCCAGCTT       1200

ACGCTTTAGA TAAATAGAAA ACTGATTAGC AGTAAAATAA GGATAATTAA GGAAAGTTGA       1260

AAATAAGCCT CATTCTGATA TTCACATTTA TATAATGAAG CTAGGATCAG CGACCTGGGG       1320

GTTTCTCTCT CTCAGGATAA ATGATTGCCT AGCGATCCTG TAGGCTGATT CATCACTCTC       1380

ACTGTTGTCT GCTTCTGCTT CTCTTTTTCA GTGTCTCAGT GCCTGAGTCC TGGGCCAAAT       1440

TTACAGATGA CATATTCTCC GCTCCCAGAG TGAACGGGCA GCTTCGCTAA GCTAAGAGAC       1500

GACATTGAAA ACCTCTTGGT TGTGACTGCC AATGAGATGT GGAATCAATT CAACAAAGTG       1560

AACTTGTCTT TCACCAATCG CATTGCTGAG ACTGCAGATG CTAAGAATAA GATTCAGACG       1620

CACTTAGCAA AGGTAAATCA ACCGCCAGTG GTACCCCTTA GCTGACCTGG ACAGAGCGGT       1680

GTGCTCTGGG ACTACAAATC TCTCACCACT CCCAGAGAGG CACCATAGGC ATGTGACAGC       1740

CTGGCCACAC AGAGCAAGAA AAATTTAAAA CAGCACAAAG CATGCCATTT ATTTCAGCCA       1800

GGTAGCCAGG TGTCAAAATG AAATTGGAAT CCACTGGTAT TTGGAACACA AAGAAGGCAC       1860

TATGTAATGA AAAGTTCTTA GTCTTTAATA GAAACAAAAA TATTATTATT AAAGTTTAAT       1920

GGATCGCTGT ATATAACTAG GAAGTGAATT TATTATTAGA ACATATGGTA GAAATGTTTT       1980

CTGTTAAAGT ATTTTAGACC CCTTTTCTGG AATACAAAAC CAAATACAGG AAACTGTTAG       2040

GTAGTTCAAA GTGTTTCTGA TATTGAAAAA TTTTAAGTGC TGAAAGCATA AGAGTTTTAC       2100

AATGACTACA AAATGAAGGA GTCCAGCAGA ATT                                    2133

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CATACAATGC ACGCAGTTGA                                                     20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:
```

AAACCCAGAA CTTCCACTTC                                                         20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TTGGTACAAC CTTCCTGGAG                                                         20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CAAATCCTGC CCATGAAGTT                                                         20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

ATGTATTGGG CTGGTTACTG                                                         20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATCCATTCAT CCATTCTCCC                                                         20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CAACATCAGG TCAACCAGAG                                                         20